United States Patent [19]

Huang et al.

[11] Patent Number: 5,418,147
[45] Date of Patent: May 23, 1995

[54] GLYCOSYL-PHOSPHATIDYLINOSITOL-SPECIFIC PHOSPHOLIPASE D

[75] Inventors: Kuo-Sen Huang, Livingston; Jarema P. Kochan, Verona; Shirley H. Li, Glen Ridge; Yu-Ching E. Pan, Pine Brook, all of N.J.; Bernard J. Scallon, Frazer, Pa.; Thomas C. H. Tsang, Belleville, N.J.

[73] Assignee: Hoffmann-La Roche Inc., Nutley, N.J.

[21] Appl. No.: 860,825

[22] Filed: Mar. 31, 1992

Related U.S. Application Data

[63] Continuation-in-part of Ser. No. 588,896, Sep. 27, 1990, abandoned.

[51] Int. Cl.$^6$ .................. C12N 9/20; C12N 15/00; B12P 21/06
[52] U.S. Cl. .................. 435/69.1; 435/198; 435/68.1; 435/69.7; 435/320.1; 435/69.8; 435/252.3; 935/47; 935/48; 536/23.2; 536/23.4
[58] Field of Search .............. 435/198, 69.1, 68.1, 435/69.7, 320.1, 252.3, 69.8; 935/47, 48; 536/27, 23.2, 23.4

[56] References Cited

U.S. PATENT DOCUMENTS 5,109,113  4/1992  Caras et al. .................. 530/350

FOREIGN PATENT DOCUMENTS 319944  6/1989  European Pat. Off. .
477739  4/1992  European Pat. Off. .

OTHER PUBLICATIONS

Davitz et al., Science, vol. 28, Oct. 2, 1987, pp. 81–84.
Scallon et al., PNAS, vol. 86, Jul. 1989, pp. 5079–5083.
Micanovic et al., PNAS, vol. 87, Jan. 1990, pp. 157–161.
Lisanti et al., J. Cell Biol., vol. 109, Nov. 1989, pp. 2145–2156.
Sesko et al., J. Cell Biochem., Abst. Suppl. 14B, Jan.–Feb. 1990.
Honer et al., Experientia, Jun. 1990, Abst. #343, p. A 42.
Suggs et al., PNAS, vol. 78, No. 11, Nov. 1981, pp. 6613–6617.
Stieger et al., Experentia, Abstract 343:A42 (Jun. 1990).
Sesko et al., J. Cell. Biochem., Sup. 14B:265 (Jan./Feb. 1990).
Almedia et al., Bioch. Biophys. Res. Comm. 150:476–482 (Jan. 15, 1988).
Fung et al., FASEB J. 4:A1775 (Abstract) No. 474 (1990).
Low et al., Proc. Natl. Acad. Sci. USA 85:980–984 (1988).
Hereld et al., Proc. Natl. Acad. Sci. USA 85:8914–8918 (1988).
Huang et al., J. Biol. Chem. 265:17738–17745 (1990).
Scallon et al., Science 252:446–448 (1991).
Davitz et al., J. Biol. Chem. 264:13760–13765 (1989).

*Primary Examiner*—Robert A. Wax
*Assistant Examiner*—Keith D. Hendricks
*Attorney, Agent, or Firm*—George M. Gould; William H. Epstein; Catherine R. Roseman

[57] ABSTRACT

The present invention involves the protein glycosyl-phosphatidyl-specific phospholipase D (GPI-PLD) in a substantially pure form, an isolated nucleotide sequence encoding GPI-PLD, vectors containing the isolated nucleotide sequence encoding GPI-PLD, and cells transformed by a vector containing the isolated nucleotide sequence encoding GPI-PLD, also nucleotide sequences, vectors and cells comprising hybrid genes with GPI-PLD, and methods for producing secreted proteins.

9 Claims, 36 Drawing Sheets

FIG. 5A

```
                                                Met Ser Ala Phe Arg Phe Trp Ser Gly Leu  -14
GCATTGCTCGTCACCATAGGAGCGGGAGTAATGAGAGC          ATG TCT GCT TTC AGA TTC TGG TCA GGA CTG   69

Leu Met Leu Gly Phe Leu Cys Pro Arg Ser Ser Pro Cys Gly Ile Ser Thr His Ile                 7
CTG ATG CTA CTG GGC TTC CTC TGC CCT AGA AGT TCA CCA TGT GGC ATT TCG ACA CAC ATA            129

Glu Ile Gly His Arg Ala Leu Glu Phe Leu His Leu Arg Gln Asp Gly Ser Ile Asn Tyr Lys         27
GAA ATA GGA CAC AGA GCT CTG GAG TTT CTC CAC CTT CAG GAT GGG AGT ATT AAC TAC AAA            189

Glu Leu Leu Arg His Gln Ala Tyr Gln Ala Gly Ser Val Phe Pro Asp Ser Phe                    47
GAG CTG TTA CTT AGG CAC CAG GAT CGA TAT CAG GCT GGA TCC GTG TTT CCT GAC TCA TTT            249

Tyr Pro Ser Ile Cys Glu Arg Gly Gln Phe His Asp Val Ser Glu Ser Thr His Trp Thr             67
TAC CCT AGC ATC TGT GAG AGA GGA CAA TTC CAT GAC GTG TCA GAG AGC ACT CAC TGG ACT            309

Pro Phe Leu Asn Ala Ser Val His Tyr Ile Arg Lys Asn Tyr Pro Leu Pro Trp Asp Glu             87
CCA TTT CTT AAC GCA AGT GTT CAT TAT ATC CGG AAG AAC TAT CCT CTT CCC TGG GAT GAG            369

Asp Thr Glu Lys Leu Val Ala Phe Leu Phe Gly Ile Thr Ser His Met Val Ala Asp Val            107
GAC ACA GAG AAA CTT GTA GCA TTT TTG GGA ATT ACG TCT CAC ATG GTG GCT GAT GTC                429

Asn Trp His Ser Leu Gly Ile Glu Gln Gly Phe Leu Arg Thr Met Ala Ala Ile Asp Phe            127
AAC TGG CAT AGC CTG GGT ATT GAA CAA GGA TTC CTT AGG ACG ATG GCT GCC ATT GAT TTT            489

His Asn Ser Tyr Pro Glu Ala His Pro Ala Gly Gly Asp Phe Gly Gly Asp Val Leu Ser Gln        147
CAC AAC TCC TAT CCC GAG GCA CAT CCG GCT GGT GAT TTC GGA GGA GAC GTG TTG AGC CAG            549

Phe Glu Phe Lys Phe Asn Try Leu Ser Arg His Trp Tyr Val Pro Ala Glu Asp Leu Leu            167
TTC GAG TTT AAA TTT AAT TAC CTC TCA CGG CAC TGG TAT GTG CCT GCT GAA GAT CTC CTG            609

Gly Ile Tyr Arg Glu Leu Try Gly Arg Ile Val Ile Thr Lys Lys Ala Ile Val Asp Cys            187
GGA ATT TAT AGA GAA CTC TAC GGC CGA ATA GTC ATC ACC AAA AAA GCC ATT GTT GAC TGT            669

Ser Try Leu Gln Phe Leu Glu Met Tyr Ala Glu Met Leu Ala Ile Ser Lys Leu Try Pro            207
TCA TAC CTT CAA TTC TTG GAA ATG GCG GAG ATG TTA GCT ATT TCC AAG CTT TAT CCC                729
```

```
Thr Tyr Ser Val Lys Ser Pro Phe Leu Val Glu Gln Phe Gln Glu Tyr Phe Leu Gly Gly 227
ACT TAT TCT GTA AAA TCC CCA TTT TTG GTG GAA CAA TTT CAA GAA TAC TTC CTA GGA GGG 789

Leu Glu Asp Met Ala Phe Trp Ser Thr Asn Ile Tyr His Leu Thr Ser Tyr Met Leu Lys 247
CTG GAA GAT ATG GCG TTT TGG TCC ACT AAT ATT TAC CAT CTG ACA AGT TAC ATG TTA AAG 849

Asn Gly Thr Ser Asn Cys Asn Pro Glu Asn Leu Pro Leu Phe Ile Thr Cys Gly Gln 267
AAC GGG ACC AGT AAT TGC AAC CCT GAG AAC CTC CCT CTG TTC ATC ACA TGT GGC GGT CAA 909

Gln Asn Asn Thr His Gly Ser Val Gln Lys Val Gln Lys Asn Gly Phe His Lys Asn Val Thr Ala 287
CAA AAC AAC ACC CAT GGC TCA AAA GTA CAG AAA AAT GGT TTT CAT AAA AAT GTG ACT GCA 969

Ala Leu Thr Lys Asn Ile Gly Lys His Ile Asn Tyr Thr Lys Arg Gly Val Phe Phe Ser 307
GCC CTA ACT AAA AAT ATT GGA AAG CAT ATA AAC TAT ACC AAA AGA GGA GTG TTC TTT AGT 1029

Val Asp Ser Trp Thr Met Asp Phe Leu Ser Phe Met Tyr Lys Ser Leu Glu Arg Ser Ile 327
GTG GAT TCC TGG ACC ATG GAT TCC TTA TCC TTC ATG TAC AAG TCT TTG GAG AGG AGT ATA 1089

Arg Glu Met Phe Ile Gly Ser Ser Gln Pro Leu Thr Ala Cys His Val Ser Ser Pro Ala Ala Ser 347
CGG GAG ATG TTT ATT GGC AGC TCT CAG CCA CTG ACA CAT GTT TCT AGC CCC GCA GCA TCT 1149

Tyr Tyr Leu Ser Phe Pro Tyr Thr Arg Leu Gly Trp Ala Met Thr Ser Ala Asp Leu Asn 367
TAC TAC TTG TCA TTT CCC TAC ACA AGG CTT GGT TGG GCA ATG ACT TCA GCT GAT CTC AAC 1209

Gln Asp Gly Tyr Gly Asp Leu Val Val Gly Ala Pro Gly Tyr Ser His Pro Gly Arg Ile 387
CAG GAT GGA TAC GGT GAC CTG GTG GTG GGT GCC CCT GGC TAC AGC CAC CCA GGC CGG ATT 1269

His Val Gly Arg Val Tyr Leu Ile Tyr Gly Asn Asp Leu Pro Leu Gly Asp Leu Asp Leu 407
CAC GTG GGG CGC GTG TAC CTC ATC TAT GGC AAT GAC CTG CCC CTG GGC TTG GAC CTG 1329

Asp Lys Leu Glu Lys Glu Ala His Gly Ile Leu Glu Leu Pro Ser Gly Arg Phe Gly 427
GAC AAG CTG GAG AAG GAG GCC CAC GGG ATC CTG GAG CCC TCA GGT TTC CGA TTT GGC 1389
```

FIG. 5B

```
Ser Ala Val Ala Val Leu Asp Phe Asn Val Asp Gly Val Pro Asp Leu Ala Val Gly Ala    247
TCG GCT GTG GCT GTG CTA GAC TTT AAC GTG GAT GGC GTG CCT GAC CTG GCT GTG GGA GCC   1449

Pro Ser Val Gly Ser Glu Lys Leu Thr Tyr Thr Gly Ala Val Tyr Val Tyr Phe Gly Ser    467
CCC TCG GTG GGC TCC GAG AAG CTC ACA TAC ACA GGT GCA GTG TAT GTC TAC TTC GGT TCC   1509

Lys Gln Gly Gln Leu Ser Ser Pro Asn Val Thr Ile Ser Cys Gln Asp Thr Tyr Cys        487
AAA CAA GGA CAA CTA TCT TCT CCC AAC GTC ACC ATC TCT TGC CAG GAT ACC TAC TGT       1569

Asn Leu Gly Trp Thr Leu Leu Ala Ala Asp Val Asn Gly Asp Ser Glu Pro Asp Leu Val    507
AAC TTG GGC TGG ACC CTC CTG GCG GCA GAT GTG AAT GGA GAT AGT GAA CCG GAC CTG GTG   1629

Ile Gly Ser Pro Phe Ala Phe Gly Gly Gly Lys Gln Lys Val Ala Ala Phe Tyr            527
ATT GGC TCC CCT TTT GCT TTT GGT GGA GGG AAA CAG AAG GTG GCT GCA TTT TAC           1689

Ser Gly Ser Ser Tyr Ser Ser Arg Glu Lys Leu Asn Val Glu Ala Ala Asn Trp Met Val    547
TCT GGC TCC AGT AGC TAC AGC AGA GAA AAG CTG AAT GTG GAG GCT GCC AAC TGG ATG GTG   1749

Lys Gly Glu Asp Phe Ala Trp Leu Gly Tyr Ser Leu His Gly Val Asn Val Asn Asn        567
AAA GGC GAG GAC TTT GCT TGG TTG GGG TAC TCC CTT CAC GGT GTC AAT GTC AAC AAC       1809

Arg Thr Leu Leu Leu Ala Gly Ser Pro Thr Trp Lys Asp Thr Ser Ser Gln Gly His Leu    587
AGG ACT TTG CTC CTG GCT GGA AGC CCG ACC TGG AAG GAC ACC AGT AGT CAG GGC CAC TTG   1869

Phe Arg Thr Arg Asp Glu Lys Gln Ser Pro Gly Arg Val Tyr Gly Tyr Phe Pro Pro Ile    607
TTC CGC ACT CGT GAT GAG AAA CAG AGC CCT GGA CGG GTG TAC GGC TAT TTC CCG CCA ATC   1929

Cys Gln Ser Trp Phe Thr Ile Ser Gly Asp Lys Ala Met Gly Lys Leu Gly Thr Ser Leu    627
TGT CAA AGC TGG TTT ACC ATT TCC GGA GAC AAG GCA ATG GGG AAA CTG GGT ACC TCC CTG   1989

Ser Ser Gly His Val Ile Val Asn Gly Thr Arg Thr Gln Val Leu Leu Gly Val Ala Pro    647
TCT AGT GGC CAC GTG ATC GTG AAC GGA ACC CGG ACC CAA GTG CTG CTG GGG GCC CCG      2049
```

FIG. 5C

```
Thr Gln Asp Val Val Ser Lys Val Ser Phe Leu Thr Met Thr Leu His Gln Gly Gly Ser  667
ACT CAA GAT GTC GTG TCT AAG GTA TCA TTC CTG ACC ATG ACC CTG CAC CAA GGT GGG AGC  2109

Thr Arg Met Tyr Glu Leu Thr Pro Asp Ser Gln Pro Ser Leu Leu Ser Thr Phe Ser Gly  687
ACT CGG ATG TAT GAA CTG ACA CCT GAC TCA CAG CCT TCT CTG CTC AGC ACC TTC AGT GGA  2169

Asn Arg Arg Phe Ser Arg Phe Gly Gly Val Leu His Leu Ser Asp Leu Asp Asn Asp Gly  707
AAC CGC CGC TTC TCC CGA TTT GGT GGC GTT CTG CAC TTG AGT GAC TTG GAT AAT GAT GGC  2229

Leu Asp Glu Ile Ile Val Ala Ala Pro Leu Arg Ile Thr Asp Ala Thr Ala Gly Leu Met  727
TTA GAT GAA ATC ATC GTA GCA GCC CCG CTG AGG ATC ACA GAC GCA ACT GCG GGA CTG ATG  2289

Gly Glu Asp Gly Arg Val Tyr Val Phe Asn Gly Lys Gln Ile Thr Val Gly Asp Val Val  747
GGG GAA GAG GAT GGC CGT GTT TAT GTG TTT AAT GGC AAA CAG ATC ACC GTG GGT GAC GTG  2349

Thr Gly Lys Cys Lys Ser Trp Val Thr Pro Cys Pro Glu Glu Lys Ala Gln Tyr Val Leu  767
ACA GGC AAA TGC AAA TCA TGG GTA ACT CCG TGT CCA GAA GAA AAG GCC CAA TAT GTA CTA  2409

Ile Ser Pro Glu Ala Gly Ser Arg Phe Gly Ser Ser Arg Val Ile Thr Val Arg Ser Lys Glu  787
ATT TCT CCT GAA GCA GGC TCA AGG TTT GGG AGC TCT AGG GTC ATC ACT GTG AGG TCG AAG GAA  2469

Lys Asn Gln Val Ile Ala Ala Ile Ile Ala Gly Leu Ala Arg Leu Ser Gly Val  807
AAG AAT CAA GTC ATC ATT GCT GCA ATT ATT GCT GGA CTG GCC CGA CTC TCT GGG GTG  2529

Leu His Ile Tyr Arg Leu Gly Gln Asp End  816
CTT CAT ATC TAT AGG CTC GGC CAA GAT TAA  AGT TTC ACT CCA TTT TCC  2578
```

FIG. 5D

NUCLEOTIDE SEQUENCE AND DEDUCED AMINO ACID SEQUENCE OF
HUMAN LIVER GPI-PHOSPHOLIPASE D cDNA

```
cgtcattagagagaggagccgtggggaatgagagcATGTCTGCTTTCAGGTTGTGGCCCGGCC   28
-----+---------+---------+---------+---------+---------+
gcagtaatctcctcgccacccccttactctgTACAGACGAAAGTCCAACACCGGGCCGG
                                 M  S  A  F  R  L  W  P  G  L     -15
                                -24
                                  1

TGCTGATGATCGTGATGGCTTCTCTCTGCCATAGAGGTTCATCGTGTGGCCCTTTCAACGC    88
-----+---------+---------+---------+---------+---------+
ACGACTACTAGCACTACCGAAGAGAGACGGTATCTCCAAGTAGCACACCGGAAAGTTGCG
 L  M  I  V  M  A  S  L  C  H  R  G  S  S  C  G  L  S  T  H       +6

ACATAGAAATCGGACACAGAGCTCTGGAGTTTCTTCATCTTCACAATGGGCATGTTAACT    148
-----+---------+---------+---------+---------+---------+
TGTATCTTTAGCCTGTGTCTCGAGACCTCAAAGAAGTAGAAGTGTTACCCGTACAATTGA
 I  E  I  G  H  R  A  L  E  F  L  H  L  H  N  G  H  V  N  Y      26

ACAAAGAGCTGTTACTAGAACACCAGGATGCATATCAGGCTGGAACCGTGTTTCCTGATT   208
-----+---------+---------+---------+---------+---------+
TGTTTCTCGACAATGATCTTGTGGTCCTACGTATAGTCCGACCTTGGCACAAAGGACTAA
 K  E  L  L  L  E  H  Q  D  A  Y  Q  A  G  T  V  F  P  D  C      46
```

FIG. 9A

```
GTTTTACCCTAGCCTCTGCAAAGGAGGAAAATTCCATGATGTGTCTGAGAGCACTCACT   268
----+----|----+----|----+----|----+----|----+----|----+----|
CAAAATGGGATCGGAGACGTTTCCTCCTTTAAGGTACTACACAGACTCTCGTGAGTGA

F  Y  P  S  L  C  K  G  G  K  F  H  D  V  S  E  S  T  H  W    66

GGACTCCGTTTCTTAACGCAAGCCGTTCATTATATCCGAGAGAACTATCCCCTTCCCTGGG   328
----+----|----+----|----+----|----+----|----+----|----+----|
CCTGAGGCAAAGAATTGCGTTCGCAAGTAATATAGGCTCTCTTGATAGGGGAAGGGACCC

T  P  F  L  N  A  S  V  H  Y  I  R  E  N  Y  P  L  P  W  E    86

AGAAGGACACAGAGAAACTGGTAGCTTT CTTGTTTGGAATTACTTCTCATATGGTAGCAG   388
----+----|----+----|----+----|----+----|----+----|----+----|
TCTTCCTGTGTCTCTTTGACCATCGAAAGAACAAACCT TAATGAAGAGTATACCATCGTC

```
ATGTCAGCTGGCATAGTCTGGGCATTGAACAAGGATTCCTTAGGACCATGGGAGCTATTG  448
----+----+----+----+----+----+----+----+----+----+----+----+
TACAGTCGACCGTATCAGACGCGTAACTTGTTCCTAAGGAATCCTGGTACCCTCGATAAC
     V  S  W  H  S  L  G  I  E  Q  G  F  L  R  T  M  G  A  I  D   126

ATTTTCACGGCTCCTATTCTGAGGCTCATTCAGCTGTGATTTTGGAGGAGATGTGTTGA  508
----+----+----+----+----+----+----+----+----+----+----+----+
TAAAAGTGCCGAGGATAAGACTCCGAGTAAGTCGACCACTAAAACCTCCTCTACACAACT
     F  H  G  S  Y  S  E  A  H  S  A  G  D  F  G  G  D  V  L  S   146

GCCAGTTTGAATTTAATTTAATTACCTTGCACGACGCTGTGGTATGTGCCAGTCAAAGATC  568
----+----+----+----+----+----+----+----+----+----+----+----+
CGGTCAAACTTAAATTAAAATTAATGGAACGTGCTGCGACCATACACGGTCAGTTCTAG
     Q  F  E  F  N  F  N  Y  L  A  R  R  W  Y  V  P  V  K  D  L   166

TGCTGGGAATTTATGAGAAACTCTATGGTCGAGAAGTCATCACTGAAAATGTAATTGTTG  628
----+----+----+----+----+----+----+----+----+----+----+----+
ACGACCCTTAAATACTCTTTGAGATACCAGCTCTTCAGTAGTGACTTTTACATTAACAAC
     L  G  I  Y  E  K  L  Y  G  R  E  V  I  T  E  N  V  I  V  D   186

ATTGTTCACATATCCAGTTCTTAGAAATGTATGGTGAGATGCTAGCTGTGTTCCAAGTTAT  688
----+----+----+----+----+----+----+----+----+----+----+----+
TAACAAGTGTATAGGTCAAGAATCTTTACATACCACTCTACGATCGACACAAGGTTCAATA
```

FIG. 9C

```
C  S  H  I  Q  F  L  E  M  Y  G  E  M  L  A  V  S  K  L  Y  206
ATCCCTCTTACTCTACAAAGTCCCCGTTTTGGTGGAACAATTCCAAGAGTATTTCTTG
         +         +         +         +         +         +  748
TAGGGAGAATGAGATGTTTCAGGGGCAAAACCACCTTGTTAAGGTTCTCATAAAGAAC

P  S  Y  S  T  K  S  P  F  L  V  E  Q  F  Q  E  Y  F  L  G  226
GAGGACTGGATGATATGGCGTTTTGGTCCACTAATATTACCATCTAACGAGCTTCATGT
         +         +         +         +         +         +  808
CTCCTGACCTACTATACCGCAAAACCAGGTGATTATAATGGTAGATTGCTCGAAGTACA

G  L  D  D  M  A  F  W  S  T  N  I  Y  H  L  T  S  F  M  L  246
TGGAGAATGGGACCAGTGACTGCAGCCTGAGAACCCTCTGTTCATTGCATGTGGTG
         +         +         +         +         +         +  868
ACCTCTTACCCTGGTCACTGACGTCGGACTCTTGGGAGACAAGTAACGTACACCAC

E  N  G  T  S  D  C  S  L  P  E  N  P  L  F  I  A  C  G  G  266
GCCAGCAAAACCACACCCAGGGCTCGAAATGCAGAAAAATGATTTTCACAGAAATTTGA
         +         +         +         +         +         +  928
CGGTCGTTTTGGTGTGGGTCCCGAGCTTTACGTCTTTTTACTAAAAGTGTCTTTAAACT

```
CTTCATCCCTAACTGAAAACATTGACAGGAATATAAACTATACCGAAAGAGGAGTGTTCT         988
     ----+---------+---------+---------+---------+---------+
GAAGTAGGGATTGACTTTTGTAACTGTCCTTATATTTGATATGGCTTTCTCCTCACAAGA

S  S  L  T  E  N  I  D  R  N  I  N  Y  T  E  R  G  V  F  F         306

TCAGTGTAAATTCCTGGACCCCGGATTCCATGTCCTTATCTACAAGGCTTTGGAAGGA         1048
     ----+---------+---------+---------+---------+---------+
AGTCACATTTAAGGACCTGGGGCCTAAGGTACAGGAAATAGATGTTCCGAAACCTTCCT

S  V  N  S  W  T  P  D  S  M  S  F  I  Y  K  A  L  E  R  N         326

ACGTAAGGACACAATGTTCATAGGTGGCTCTCAGTTGTCACAGAAGCACATCTCTAGCCCCT     1108
     ----+---------+---------+---------+---------+---------+
TGCATTCCTGTGTTACAAGTATCCACCGAGAGTCAACAGTGTCTTCGTGTAGAGATCGGGGA

V  R  T  M  F  I  G  G  S  Q  L  S  Q  K  H  I  S  S  P  L         346

TAGCATCTTACTTCTGTCATTTCCTATGCAAGGCTTGGCTGGGCAATGACCTCAGCTG         1168
     ----+---------+---------+---------+---------+---------+
ATCGTAGAATGAAGACAGTAAAGGAATACGTTCCGAACGACCCGTTACTGGAGTCGAC

A  S  Y  F  L  S  F  P  Y  A  R  L  G  W  A  M  T  S  A  D         366

ACCTCAACCAGGATGGGTACGGCGACCTCGTGGTGGGCGCCAGGCTACAGCCGCCCTG         1228
     ----+---------+---------+---------+---------+---------+
TGGAGTTGGTCCTACCCATGCCGCTGGAGCACCACCCGGTGGTCCGATGTCGGCGGGAC

```
GCCGCATCCACATCGGGCGCCGTGTACCTCATCTACGGCAATGAACTGGGTCTGCCGCCG        1288
        -----+---------+---------+---------+---------+---------+
CGGCGTAGGTGTAGCCCGCGGCACATGGAGTAGATGCCGTTACTTGACCCAGACGGCGGGC

R   I   H   I   G   R   V   Y   L   I   Y   G   N   E   L   G   L   P   P   V    406

TTGACCTGGACCTGGACAAGGAGCCCACGGATCCTTGAAGGTTCCAGCCCTCAGGTC          1348
        -----+---------+---------+---------+---------+---------+
AACTGGACCTGGACCTGTTCCTCCGGGTGCCCTAGGAACTTCCAAAGGTCGGGAGTCCAG

D   L   D   L   D   K   E   A   H   G   I   L   E   G   F   Q   P   S   G   R    426

GGTTTGGCTCGGCCTTGGCTATGTTGGACTTTAACATGGATGGCGTGCCTGACCTGGCCG        1408
        -----+---------+---------+---------+---------+---------+
CCAAACCGAGCCGGAACCGATACAACCTGAAATTGTACCTACCGCACGGACTGGACCGGC

F   G   S   A   L   A   M   L   D   F   N   M   D   G   V   P   D   L   A   V    446

TGGGAGCTCCCTCGGTGGGCTCTGAGCAGTCACCTACAAAGGTGCTGTGTATGTCTACT        1468
        -----+---------+---------+---------+---------+---------+
ACCCTCGAGGGAGCCACCCGAGACTCGTCAGTGGATGTTTCCACGACACATACAGATGA

```
TTGGTTCCAAACAAGGAAGAATGTCTTCTTCCCTAACATCACCATCTCTTGCCAGGACA       1528
    ----+----|----+----|----+----|----+----|----+----|----+----|
AACCAAGGTTTGTTCCTTCTTACAGAAGAAGGGATTGTAGTGGTAGAGAACGGTCCTGT
  G  S  K  Q  G  R  M  S  S  S  P  N  I  T  I  S  C  Q  D  I        486

TCTACTGTAACTTGGGCTGGACTCTCTTGGCTGCAGATGTGAATGGAGACAGTGAGCCCG       1588
    ----+----|----+----|----+----|----+----|----+----|----+----|
AGATGACATTGAACCCGACCTGAGAGAACCGACGTCTACACTTACCTCTGTCACTCGGGC
  Y  C  N  L  G  W  T  L  L  A  A  D  V  N  G  D  S  E  P  D        506

ATCTGGTCATTGGCTCTCCCCTTTGCACCAGGTGGAGGAAGCAGAAGGAATTGTGGCTG        1648
    ----+----|----+----|----+----|----+----|----+----|----+----|
TAGACCAGTAACCGAGAGGGGAAACGTGGTCCACCTCCTTCGTCTTCCTTAACACCGAC
  L  V  I  G  S  P  F  A  P  G  G  G  K  Q  K  G  I  V  A  A        526

CGTTTTATTCTGGCCCCAGCCTGAGCAACAAAGAGAAACTGAACGTGGAGGCGGCCAACT       1708
    ----+----|----+----|----+----|----+----|----+----|----+----|
GCAAAATAAGACCGGGGTCGGACTCGTTGTTCTCTTTGACTTGCACCTCCGCCGGTTGA
  F  Y  S  G  P  S  L  S  N  K  E  K  L  N  V  E  A  A  N  W        546

GGACGGTGAGAGGCGAGAAGACTTTGCCTGGTTTGGATACTCCCTTCACGGTGTCACTG        1768
    ----+----|----+----|----+----|----+----|----+----|----+----|
CCTGCCACTCTCCGCTCCTTCTGAAACGGACCAAACCTATGAGGGAAGTGCCACAGTGAC
  T  V  R  G  E  E  D  F  A  W  F  G  Y  S  L  H  G  V  T  V        566
```

FIG. 9G

```
TGGACAACAGAACCTTGCTGCTGGTTGGGAGCCCGACCTGGAAGAATGCCAGCAGGCTGG
----------+---------+---------+---------+---------+---------+  1828
ACCTGTTGTCTTGGAACGACGACCAACCCTCGGGCTGGACCTTCTTACGGTCGTCCGACC

D  N  R  T  L  L  L  V  G  S  P  T  W  K  N  A  S  R  L  G     586

GCCGTTTGTTACACATCCGAGATGAGAAAAAGAGCCTTGGGAGGGTGTATGGCTACTTCC
----------+---------+---------+---------+---------+---------+  1888
CGGCAAACAATGTGTAGGCTCTACTCTTTTTCTCGGAACCCTCCCACATACCGATGAAGG

R  L  H  I  R  D  E  K  K  S  L  G  R  V  Y  G  Y  F  P       606

CACCAAACAGCCAAAGCTGGTTTACCATTGTTGGAGACAAGGCAATGGGGAAACTGGGTA
----------+---------+---------+---------+---------+---------+  1948
GTGGTTTGTCGGTTTCGACCAAATGGTAACAACCTCTGTTCCGTTACCCCTTTGACCCAT

P  N  S  Q  S  W  F  T  I  V  G  D  K  A  M  G  K  L  G  T    626

CTTCCCTGTCCAGTGGCCACGTGCTGATGAATGAACTCTGACCCAGGTGCTGCTGGTGG
----------+---------+---------+---------+---------+---------+  2008
GAAGGGACAGGTCACCGGTGCACGACTACTTACCTTGAGACTGGTCCACGACGACCACC

```
GAGCCCCGACACGTGATGATGTGTCTAAGATGGCATTCCTGACCATGACCCTGCACCAAG
     ----+----+----+----+----+----+----+----+----+----+----+----+  2068
CTCGGGGCTGTGCACTACTACACAGATTCTACCGTAAGGACTGGTACTGGGACGTGGTTC

A  P  T  R  D  D  V  S  K  M  A  F  L  T  M  T  L  H  Q  G   666

GCGGAGCCACTCGGATGTACGCGCTCACATCCGACCTGCAGCCACCGCTCCTGCTCAGCACCT
     ----+----+----+----+----+----+----+----+----+----+----+----+  2128
CGCCTCGGTGAGCCTACATGCGCGAGTGTAGGCTGGACGTCGGTGGCGACGAGTCGTGGA

G  A  T  R  M  Y  A  L  T  S  D  L  Q  P  P  L  L  S  T  F   686

TCAGCGGAGACCGCCGCCCGCTTCTCTCGATTTGGTGGTTCTGCACTTGAGTGACCTGGATG
     ----+----+----+----+----+----+----+----+----+----+----+----+  2188
AGTCGCCCTCTGGCGGCGGGCGAAGAGAGCTAAACCACCGAAGACGTGAACTCACTGGACCTAC

S  G  D  R  R  F  S  R  F  G  G  V  L  H  L  S  D  L  D  D   706

ATGATGGCGTAGATGAAATCATCGTGGCCAGCCCCCTGAGGATAGCAGATGTAACCTCTG
     ----+----+----+----+----+----+----+----+----+----+----+----+  2248
TACTACCGCATCTACTTTAGTAGCACCGTCGGGGGACTCCTATCGTCTACATTGGAGAC

D  G  V  D  E  I  I  V  A  A  P  L  R  I  A  D  V  T  S  G   726

GGCTGATTGGGGGAGAAGATGGCCGAGTTTATGTATATAATGCAAAGAGACCACCCTTG
     ----+----+----+----+----+----+----+----+----+----+----+----+  2308
CCGACTAACCCCCTCTTCTACCGGCTCAAATACATATATTACCGTTTCTCTGGTGGGAAC

```
GTGACATGACTGGCAAATCGTGGATGACTCCATGTCCAGAAGAAAGGCCCAAT
      ----+----+----+----+----+----+----+----+----+----+----+    2368
CACTGTACTGACCGTTTAGCACCTACTGAGGTACAGGTCTTCTTTCCGGGTTA

D   M   T   G   K   C   K   S   W   M   T   P   C   P   E   E   K   A   Q   Y    766

ATGTATTGATTTCTCCTGAAGCCAGCTCAAGGTTTGGGAGCTCCCTGATCACCGTGAGGT
      ----+----+----+----+----+----+----+----+----+----+----+    2428
TACATAACTAAAGAGGACTTCGGTCGAGTTCCAAACCCTCGAGGGACTAGTGGCACTCCA

V   L   I   S   P   E   A   S   S   R   F   G   S   S   L   I   T   V   R   S    786

CCAAGGCAAAGAATCAAGTCGTCATTGCCGCTGGAAGGAGCTCTTTGGGAGCCCGACTCT
      ----+----+----+----+----+----+----+----+----+----+----+    2488
GGTTCCGTTTCTTAGTTCAGCAGTAACGGCGACCTTCCTCGAGAAACCCTCGGGCTGAGA

K   A   K   N   Q   V   V   I   A   A   G   R   S   S   L   G   A   R   L   S    806

CCGGGGCACTTCACGTCTATAGCCTTGGCTCAGATTGA
      ----+----+----+----+----+----+----    2526
GGCCCCGTGAAGTGCAGATATCGGAACCGAGTCTAACT

G   A   L   H   V   Y   S   L   G   S   D   STOP                                   817
```

FIG. 9J

ALIGNMENT OF DEDUCED AMINO ACID SEQUENCE OF
HUMAN AND BOVINE LIVER GPI-PHOSPHOLIPASE D

```
            -24                                                              25
BOVINE      MSAFRFWSGL  LMLL.GFLCP  RSSP.CGIST  HIEIGHRALE  FLHLQDGSIN
HUMAN       MSAFRLWPGL  LMIVMASLCH  RGSS.CGLST  HIEIGHRALE  FLHLHNGHVN
            MSAFR.W.GL  LM.....LC.  R.S..CG.ST  HIEIGHRALE  FLHL..G..N 26                                                               75
BOVINE      YKELLRHQD   AYQAGSVFPD  SFYPSICERG  QFHDVSESTH  WTPFLNASVH
HUMAN       YKELLEHQD   AYQAGTVFPD  CFYPSLCKGG  KFHDVSESTH  WTPFLNASVH
            YKELL.HQD   AYQAG.VFPD  .FYPS.C..G  .FHDVSESTH  WTPFLNASVH 76                                                               125
BOVINE      YIRKNPLPW   DEDTEKLVAF  LFGITSHMVA  DVNWHSLGIE  QGFLRTMAAI
HUMAN       YIRENPLPW   EKDTEKLVAF  LFGITSHMVA  DVSWHSLGIE  QGFLRTMGAI
            YIR.NPLPW   ..DTEKLVAF  LFGITSHMVA  DV.WHSLGIE  QGFLRTM.AI 126                                                              175
BOVINE      DFHNSYPEAH  PAGDFGGDVL  SQFEFKFNYL  SRHWYVPAED  LLGIYRELYG
HUMAN       DFHGSYSEAH  SAGDFGGDVL  SQFEFNFNYL  ARRWYVPVKD  LLGIYEKLYG
            DFH.SY.EAH  .AGDFGGDVL  SQFEF.FNYL  .R.WYVP..D  LLGIY..LYG 176                                                              225
BOVINE      RIVITKKAIV  DCSYLQFLEV  YAEMLAISKL  YPTYSVKSPF  LVEQFQEYFL
HUMAN       REVITENVIV  DCSHIQFLEM  YGEMLAVSKL  YPSYSTKSPF  LVEQFQEYFL
            R.VIT...IV  DCS...QFLE  Y.EMLA.SKL  YP.YS.KSPF  LVEQFQEYFL 226                                                              275
BOVINE      GGLEDMAFWS  TNIYHLTSYM  LKNGTSNCNL  PENPLFITCG  GQQNNTHGSK
HUMAN       GGLDDMAFWS  TNIYHLTSFM  LENGTSDCSL  PENPLFIACG  GQQNHTQGSK
            GGL.DMAFWS  TNIYHLTS.M  L.NGTS.C.L  PENPLFI.CG  GQQN.T.GSK
```

```
              276
BOVINE       VQKNGFHKNV  TAALTKNIGK  HINYTKRGVF  FSVDSWTMDS  LSFMYKSLER
HUMAN        MQKNDFHRNL  TSSLTENIDR  NINYTERGVF  FSVNSWTPDS  MSFIYKALER
             .QKN.FH.N.  T..LT.NI..  .INYT.RGVF  FSV.SWT.DS  .SF.YK.LER
                                                                     325

326
BOVINE       SIREMFIGSS  Q.PLTHVSSP  AASYLSFPY   TRLGWAMTSA  DLNQDGYGDL
HUMAN        NVRTMFIGGS  QLSQKHISSP  LASYFLSFPY  ARLGWAMTSA  DLNQDGYGDL
             ..R.MFIG.S  Q....H.SSP  .ASY.LSFPY  .RLGWAMTSA  DLNQDGYGDL
                                                                     375

376
BOVINE       VVGAPGYSHP  GRIHVGRVYL  IYGNDLGLPR  IDLDLDKEAH  GILEGFQPSG
HUMAN        VVGAPGYSRP  GRIHIGRVYL  IYGNELGLPP  VDLDLDKEAH  GILEGFQPSG
             VVGAPGYS.P  GRIH.GRVYL  IYGN.LGLP.  .DLDLDKEAH  GILEGFQPSG
                                                                     425
```

|  | 426 |  |  |  | 475 |
|---|---|---|---|---|---|
| BOVINE | RFGSAVAVLD | FNVDGVPDLA | VGAPSVGSEK | LTYTGAVYY | FGSKQGQLSS |
| HUMAN | RFGSALAMLD | FNMDGVPDLA | VGAPSVGSEQ | LTYKGAVYY | FGSKQGRMSS |
|  | RFGSA.A.LD | FN.DGVPDLA | VGAPSVGSE. | LTY.GAVYY | FGSKQG..SS |

|  | 476 |  |  |  | 525 |
|---|---|---|---|---|---|
| BOVINE | SPNVTISCQD | TYCNLGWTLL | AADVNGDSEP | DLVIGSPFAP | GGGKQKGIVA |
| HUMAN | SPNITISCQD | IYCNLGWTLL | AADVNGDSEP | DLVIGSPFAP | GGGKQKGIVA |
|  | SPN.TISCQD | .YCNLGWTLL | AADVNGDSEP | DLVIGSPFAP | GGGKQKGIVA |

|  | 526 |  |  |  | 575 |
|---|---|---|---|---|---|
| BOVINE | AFYSGSSYSS | REKLNVEAAN | WMVKGEEDFA | WLGYSLHGVN | VNNRTLLLAG |
| HUMAN | AFYSGPSLSN | KEKLNVEAAN | WTVRGEEDFA | WFGYSLHGVT | VDNRTLLLVG |
|  | AFYSG.S.S. | .EKLNVEAAN | W.V.GEEDFA | W.GYSLHGV. | V.NRTLLL.G |

|  | 576 |  |  |  | 625 |
|---|---|---|---|---|---|
| BOVINE | SPTWKDTSSQ | GHLFRTRDEK | QSPGRVYGYF | PPICQSWFTI | SGDKAMGKLG |
| HUMAN | SPTWKNASRL | GRLLHIRDEK | KSLGRVYGYF | PPNSQSWFTI | VGDKAMGKLG |
|  | SPTWK..S.. | G.L...RDEK | .S.GRVYGYF | PP..QSWFTI | .GDKAMGKLG |

|  | 626 |  |  |  | 675 |
|---|---|---|---|---|---|
| BOVINE | TSLSSGHVMV | NGTRTQVLLV | GAPTQDVVSK | VSFLTMTLHQ | GGSTRMYELT |
| HUMAN | TSLSSGHVLM | NGTLTQVLLV | GAPTRDDVSK | MAFLTMTLHQ | GGATRMYALT |
|  | TSLSSGHV.. | NGT.TQVLLV | GAPT.D.VSK | ..FLTMTLHQ | GG.TRMY.LT |

FIG. 10C

```
           676
BOVINE  .PDSQPSLLST  FSGNRRFSRF  GGVLHLSDLD  NDGLDEIIVA  APLRITDATA
HUMAN    SDLQPPLLST  FSGDRRFSRF  GGVLHLSDLD  DDGVDEIIVA  APLRIADVTS    725
         .D.QP.LLST  FSG.RRFSRF  GGVLHLSDLD  .DG.DEIIVA  APLRI.D.T.

726
BOVINE   GLMGEEDGRV  YVFNGKQITV  GDVTGKCKSW  VTPCPEEKAQ  YVLISPEAGS
HUMAN    GLIGGEDGRV  YYYNGKETTL  GDMTGKCKSW  MTPCPEEKAQ  YVLISPEASS   775
         GL.G.EDGRV  YV.NGK...T. GD.TGKCKSW  .TPCPEEKAQ  YVLISPEA.S

776
BOVINE   RFGSSVITVR  SKEKNQVIIA  AGRSSLGARL  SGVLHIYRLG  QD*
HUMAN    RFGSSLITVR  SKAKNQWIA   AGRSSLGARL  SGALHVYSLG  SD*           817
         RFGSS.ITVR  SK.KNQV.IA  AGRSSLGARL  SG.LH.Y.LG  .D*
```

FIG. 10D

THE NUCLEOTIDE SEQUENCE AND AMINO ACID SEQUENCE
OF THE HUMAN PANCREATIC GLYCOSYL PHOSPHATIDYL
INOSITOL SPECIFIC–PHOSPHOLIPASE D.

```
1    GACAGTGAACCCGATCTGGTCATCGGCTCCCCTTTGCACCAGGTGGAGGAAGCAGAAG      60
1    Asp Ser Glu Pro Asp Leu Val Ile Gly Ser Pro Phe Ala Pro Gly Gly Gly Lys Gln Lys   20

61   GGAATTGTGGCTGCGT TTTATTCTGGCCCCAGCCTGAGCGACAAAGAAAACTGAACGTG    120
21   Gly Ile Val Ala Ala Phe Tyr Ser Gly Pro Ser Leu Ser Asp Lys Glu Lys Leu Asn Val   40

121  GAGGCAGCCAACTGAGACGGTGAGAGGCGAGGAAGACTTCTCCTGGTTTGGATATTCCCTT   180
41   Glu Ala Ala Asn Trp Thr Val Arg Gly Glu Glu Asp Phe Ser Trp Phe Gly Tyr Ser Leu   60

181  CACGGTGTCACTGTGGACAACAGAACCTTGCTGTTGGGTTGGGAGCCCGACCTGGAAGAAT  240
61   His Gly Val Thr Val Asp Asn Arg Thr Leu Leu Leu Val Gly Ser Pro Thr Trp Lys Asn   80

241  GCCAGCAGGCTGGGCCATTGTTACACATCCGAGATGAGAAAAGAGCCTTGGGAGGGTG     300
81   Ala Ser Arg Leu Gly His Leu His Ile Arg Asp Glu Lys Lys Ser Leu Gly Arg Val      100

301  TATGGCTACTTCCACCAAACGGCCAAAGCTGGTTTACCATTTCTGGAGACAAGGCAATG    360
101  Tyr Gly Tyr Phe Pro Pro Asn Gly Gln Ser Trp Phe Thr Ile Ser Gly Asp Lys Ala Met  120
```

FIG. 11A

```
361  GGGAAACTGGGTACTTCCCTTTCCAGTGGTCACGTACTACTGATGAATGGGACTCTGAAACAA        420
121  Gly Lys Leu Gly Thr Ser LeuSer Ser Gly His Val LeuMet Asn Gly Thr Leu Lys Gln   140

421  GTGCTGCTGGTTGGAGAGCCCCTACGATGACGTGTCTAAGGTGGCATTCCTGACCGTG            480
141  Val LeuLeu Val Gly Ala Pro Thr Tyr Asp Asp ValSerLys Val Ala PheLeu Thr Val    160

481  ACCCTACACCAAGGCGGAGCCACTCGCCTGTACGCACTCATATCTGACGCCAGCCTCTG           540
161  Thr LeuHis Gln Gly Gly Ala Thr Arg Val Tyr Ala Leu Ile SerAsp Ala Gln Pro Leu  180

541  CTGCTCAGCACCTTCAGCGGAGACCGCCGCTTCTCCCGATTGGTGGCGTTCTGCACTTG           600
181  LeuLeu Ser Thr PheSer Gly Asp Arg Arg PheSer Arg PheGly Gly Val LeuHis Leu     200

601  AGTGACCTGGATGATGATGCTTAGATGAAATCATCATGGCAGCCCCCTGAGGATAGCA            660
201  Ser Asp LeuAsp AspAsp Asp Gly LeuAspGlu Ile Ile Met Ala Ala Pro Leu Arg Ile Ala   220

661  GATGTAACCTCTGACTGATTGGGGAGAAGACGCCCAGTATATGTATATAATGGCAAA             720
221  AspVal Thr Ser Gly Leu Ile Gly Gly Gly Glu Asp Gly Arg Val Tyr Val Tyr Asn Gly Lys   240
```

FIG. 11B

```
721  GAGACCACCCTTGGTGACATGACTGGCAAATCATGGATAACTCCATGTCCAGAA           780
241  Glu Thr Thr Leu Gly Asp Met Thr Gly Lys Cys Lys Ser Trp Ile Thr Pro Cys Pro Glu   260

781  GAAAAGGCGCAATATGTATTGATTTCTCCTGAAGCTCAAGGTTTGGGAGCTCCCTC          840
261  Glu Lys Ala Gln Tyr Val Leu Ile Ser Pro Glu Ala Ser Ser Arg Phe Gly Ser Ser Leu  280

841  ATCACCGTGAGGTCCAAGGTCAAAGAACCAAGTCGTCATTGCTGCTGGAAGGAGTTCTTTG     900
281  Ile Thr Ala Arg Ser Lys Ala Lys Asn Gln Val Val Ile Ala Ala Gly Arg Ser Ser Leu  300

901  GGAGCCCGACTCTCCGGGGCACTTCACGTCTATAGCCTTGGCTCAGATTGAAGATTTCAC      960
301  Gly Ala Arg Leu Ser Gly Ala Leu His Val Tyr Ser Leu Gly Ser Asp                  320

961  TGCATTTCCCCACTCTGCCCACCTCTCTCATGCTGAATCACATCCATGGTGAGCATTTG      1020

1021 ATGGACAAAGTGGCACATCCAGTGGAGCGGGTGGTAGATCCTGATAGACATGGGGCTCCTG    1080

1081 GGAGTAGAGAGACACACTAACAGCCACACCCTCTGGAAATCTGATACAGTAAATATATGA    1140

1141 CTACACCAGAAATATGTGAAATAGCAGAGACATTCTGCTTACTCATGTCTCCTTCCACAGTT   1200

1201 TACTTCCTCGCTCCCTTTGCATCTAAACCTTTCTTCTTTCCCAACTTATTGCCTGTAGTC    1260
```

FIG. 11C

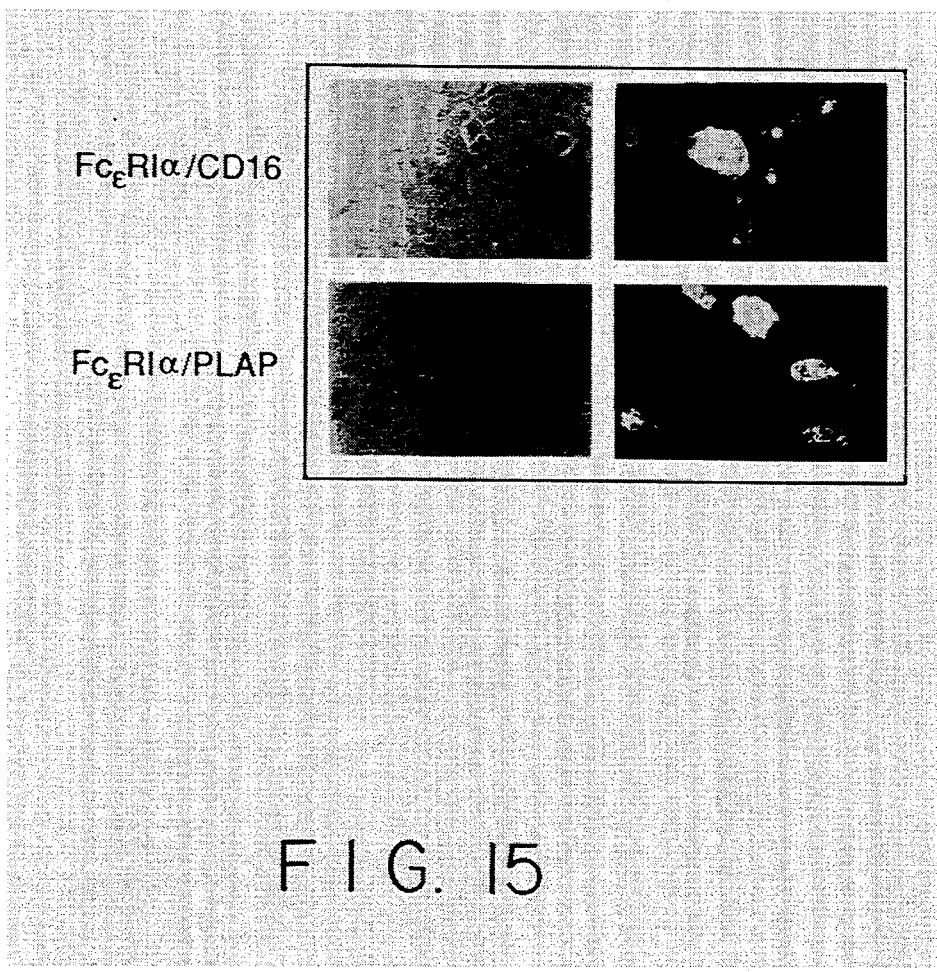
F I G. 15

GLYCOSYL-PHOSPHATIDYLINOSITOL-SPECIFIC PHOSPHOLIPASE D

This application is a continuation-in-part of U.S. Ser. No. 07/588,896, filed Sep. 27, 1990, now abandoned.

FIELD OF THE INVENTION

The present invention lies in the fields of protein, recombinant DNA, and genetic engineering.

BACKGROUND OF THE INVENTION

Recent studies have revealed that a growing number of cell surface proteins are attached to the membrane by covalent linkage to a glycosylphosphatidylinositol (GPI) (also called phosphatidylinositol-glycan (PI-G)) anchor. The physiological role played by this new class of membrane anchor is unknown, but one possibility is that it facilitates the release of molecules by specific phospholipases in vivo.

Several mammalian phospholipase activities which seem to be capable of removing the GPI anchors from proteins have been reported. These were originally attributed to the action of a phosphatidylinositol (PI)-specific phospholipase C since enzymes of this specificity are widely distributed in mammalian tissues. However, the physiological significance of such a process remained in question because almost all of the mammalian PI-specific phospholipase C's are believed to be intracellular in location whereas the GPI-anchored proteins are found on the cell surface. Subsequently, it was shown that inhibition of placental PI-specific phospholipase C activity does not affect GPI-anchor degrading activity, indicating that other enzymes are responsible for the release of GPI-anchored proteins. It was therefore suggested that this activity was due to a novel phospholipase D with specificity for the GPI-anchor. Recently, several groups have reported the presence of high levels of a GPI-specific phospholipase D (GPI-PLD), also called phosphatidylinositolglycan-specific phospholipase D in mammalian plasma and serum (6, 7, 8) Because of its extracellular location and specificity for GPI, this enzyme may be responsible for releasing GPI-anchored proteins from cell surfaces in vivo.

Secretion of proteins of interest from transfected eukaryotic cells permits the isolation and characterization of that protein free of the complex intracellular milieu and does so in the absence of detergents. Traditional methods for obtaining secretion have included attachment of secretory signal sequences to intracellular proteins or truncation of proteins to delete "retention signals" such as hydrophobic transmembrane domains. Many proteins have been successfully secreted to varying degrees using these strategies, but other proteins have remained obstinate for reasons that are usually not clear. An ideal method would be a dominant-acting post-translational modification that would specifically "tag" a protein for efficient secretion. While no such tag has yet been found, it appears that a naturally-occurring, dominant-acting modification has been identified that results in efficient cell-surface expression of the modified protein. Secretion of these proteins would then be realized by their specific release from the cell surface.

The modification referrred to is the post-translational transfer of a glycosylphosphatidylinositol (GPI) moiety to the COOH-terminal end of a protein (1,3,4,30-33). Numerous proteins in organisms ranging from trypanosomes to humans are anchored to the cell surface in this manner. The signal for GPI attachment is not completely defined by invariably includes a hydrophobic stretch of amino acids near the COOH-terminus of the initial translation product. These residues are proteolytically removed prior to en bloc attachment of the anchor (31). These GPI proteins are transported to the cell surface where the fatty acids of the GPI moiety serve to anchor the molecule to the outer leaflet of the lipid bilayer. The physiological role of this complex anchor is not clear, but proposals have included (1,3,4,33): 1) conferring on the protein high lateral mobility in the plasma membrane, and 2) generation of signal transducting molecules by a phospholipase-catalyzed hydrolysis of the GPI moiety.

Lisanti et al. (34) showed that expression of a chimeric gene encoding (at the 5' end) a protein that is normally secreted with (at the 3' end) a signal sequence; for GPI attachment resulted in the protein being localized at the cell surface. Furthermore, it can be demonstrated that GPI anchors act as dominant sorting signals by redirecting what are normally basolateral proteins to the apical side of polarized epithelial cells (1,3,4,33). While this activity can be exploited to obtain cell-surface expression of a protein of interest, it is also of interest to achieve secretion of proteins.

Molecules which are released in this way might be expected to contain a common COOH-terminus consisting of a hydrolyzed GPI anchor which is missing a phosphatidic acid moiety. The presence of a common structural epitope would facilitate the purification of these proteins. Antibodies specific for the phospholipase C cleaved GPI anchor, and anti-CRD reagents, have been previously described (33). Development of antibodies to a PLD cleaved GPI anchor would facilitate the purification of GPI PLD released GP anchored proteins.

SUMMARY OF THE INVENTION

The present invention discloses the protein glycosylphosphatidylinositol specific phospholipase D (GPI-PLD) in a substantially pure form or a biologically active fragment thereof substantially free from other proteins, an isolated nucleotide sequence encoding GPI-PLD or a biologically active fragment thereof, vectors containing the isolated nucleotide sequence encoding GPI-PLD or a biologically active fragment thereof, and cells transformed by a vector containing the isolated nucleotide sequence encoding GPI-PLD.

Also contemplated are mutations of GPI-PLD or biologically active fragments thereof which substantially retain the biological activity of natural GPI-PLD, an isolated polynucleotide encoding the mutant GPI-PLD or a biologically active fragment thereof, vectors containing the isolated polynucleotide encoding for the mutant GPI-PLD or a biologically active fragment thereof, and cells transformed by a vector containing the isolated polynucleotide encoding for the mutant GPI-PLD or biologically active fragment thereof.

A method is claimed for obtaining a secretable protein from a cell, such as a eukaryotic cell, comprising co-transfecting a cell with a nucleotide sequence encoding a glycosyl phosphatidyl inositol-anchored protein and with a nucleotide sequence encoding glycosyl phosphatidyl inositol-specific phospholipase D.

A synthetic nucleotide sequence which causes expression of a protein desired to be secreted is claimed, and also vectors and host cells which contain such a nucleotide sequence.

Also disclosed is a process for cleaving proteins which are anchored to a cell by means of a glycosyl phosphatidylinositol anchor comprising administering to the cell culture in which the cell is growing phosphatidyl inositol-specific phospholipase D in combination with a suitable detergent.

Also disclosed are antibodies specific to GPI-PLD substantially free from other proteins.

FIGS. (5a–5D) DNA sequence and deduced amino acid sequence of bovine liver GPI-PLD. The arrow marks the N-terminus of the mature protein. Regions showing sequence similarity to metal ion binding domains of integrin a subunits are underlined.

Figure 6:
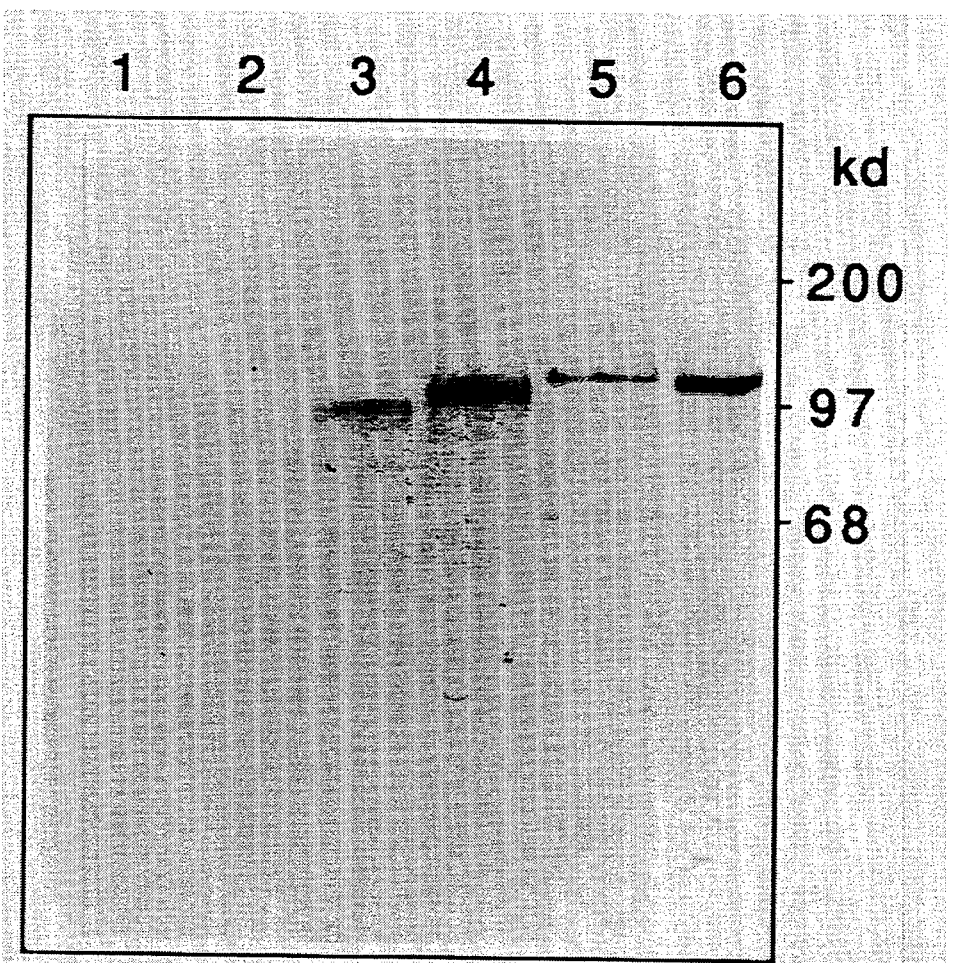

FIG. 6. Western Blot Analysis of Transfected COS Cell Media and Lysates. The complete 2.6 kb cloned cDNA was ligated into the HindIII/SmaI site of pBC12B1 and the recombinant plasmid, pBJ1682, introduced into COS-7 cells utilizing standard DEAE-dextran mediated methods. COS cells were cultured in Dulbecco's modified Eagle's medium (DMEM) containing 10% fetal calf serum for the first 24 hours then switched to serum-free DMEM containing 1% Nutridoma (Boehringer Mannheim, Indianapolis, Ind.) to rid of endogenous PLD. Media was collected 48 hours after switching to serum-free media, centrifuged to pellet any suspended cells and concentrated 15-fold using Centricon 10 (Amicon, Danvers, Mass.). Cell lysates were prepared at a concentration of $5 \times 10^7$ cell-equivalents per ml in 0.5% Nonidet P-40 in PBS containing aprotinin (30 mg/ml), leupeptin (10 μg/ml), pepstatin (10 μg/ml), and phenylmethyl sulfonyl flouride (1 mM). Lysates were centrifuged at 13,000 g for 20 min at 4° C. and the supernatant collected. After gel electrophoresis and blotting to nitrocellulose, proteins were detected using a pool of five monoclonal antibodies (1 μg/ml each) against bovine serum GPI-PLD and alkaline-phosphatase conjugated goat anti-mouse IgG (Jackson ImmunoResearch, West Grove, Pa.). Lane 1, lysate of mock-transfected cells; Lane 2, medium from mock-transfected cells; Lane 3, equal amounts of lysate from pBJ1682-transfected cells and medium from mock-transfected cells; Lane 4, equal amounts of medium from pBJ1682-transfected cells and lysate from mock-transfected cells; Lane 5, 50 ng of purified serum GPI-PLD; Lane 6, 200 ng of purified serum GPI-PLD mixed with mock-transfected cell medium.

Figures 7A, 7B:
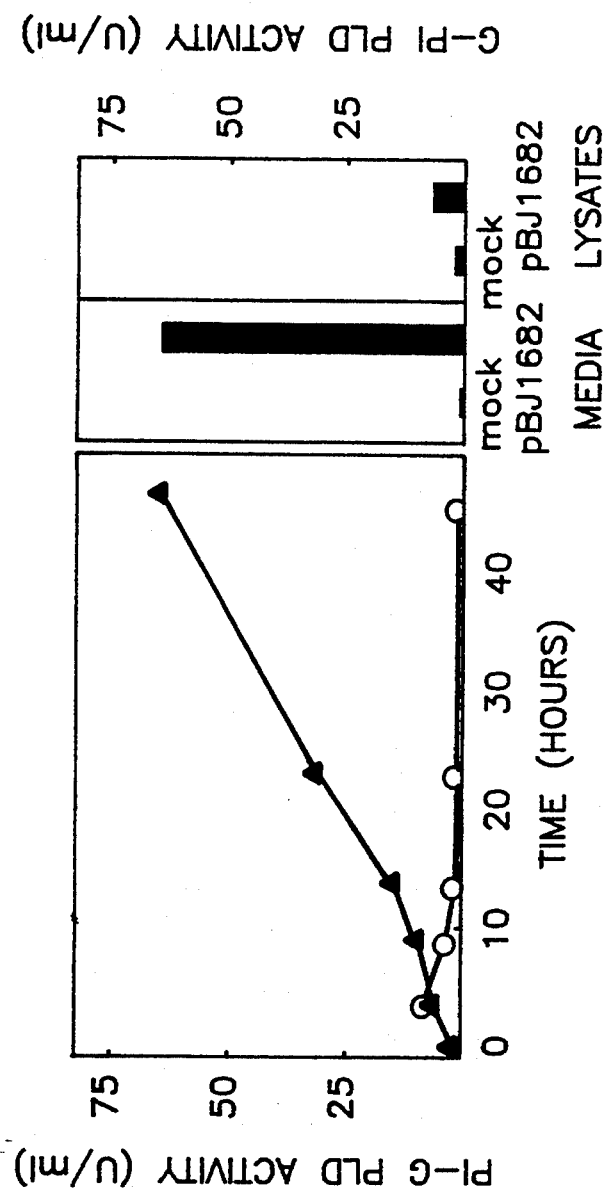

FIGS. 7A & B Demonstration of GPI-PLD Activity in Transfected COS Cells by Hydrolysis of $^3$H-labelled VSG. Mock-transfected or pBJ1682-transfected COS cells were switched to serum-free media 24 hours after transfection as described for FIG. 6. (A) Time dependence of phospholipase activity. At various time points after switching to serum-free medium, aliquots (10 μl each) were withdrawn from the medium and assayed for phospholipase activity. One unit of activity was defined as the amount of enzyme hydrolyzing 1% of the [$^3$H]myristate-labelled VSG per min. Δ ... Δ indicates the activity in DNA-transfected cells; o ... o indicates the activity in mock-transfected transfected cells. (B) Comparison of phospholipase activity in the medium and cell lysate. After cells were grown in serum-free medium for 44 hours, 10 μl of medium was withdrawn and assayed for phospholipase activity. Cells lysates were prepared as described in FIG. 6 and assayed at the same time.

Figure 8:
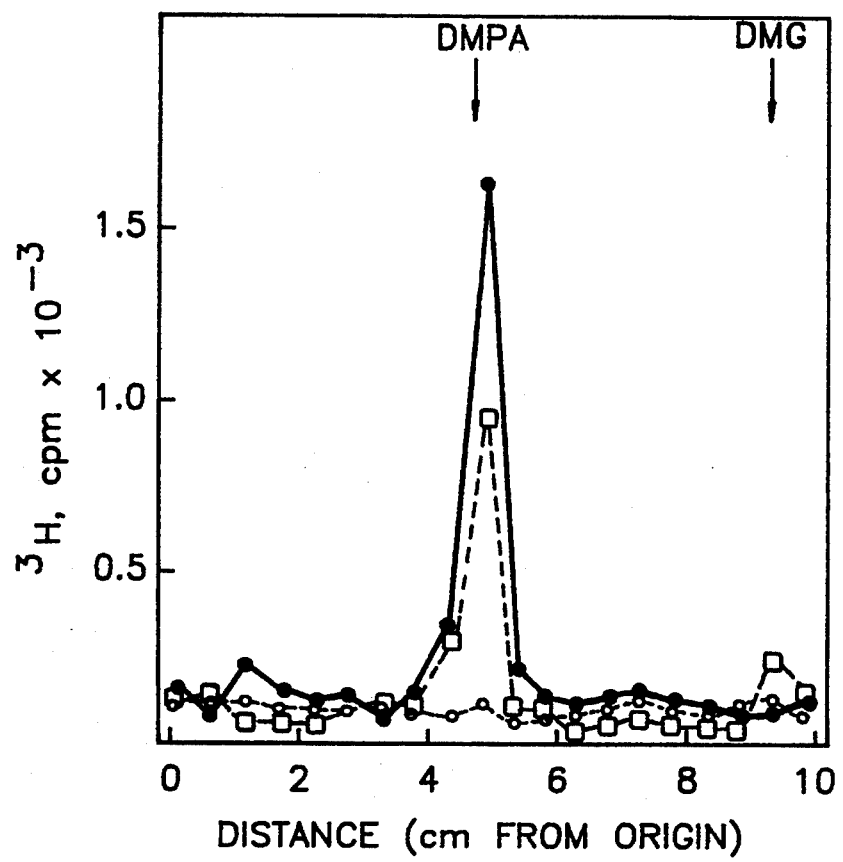

FIG. 8. Product Analysis of Hydrolyzed VSG by Thin-layer Chromatography. Samples (50 μl) of pBJ1682- and mock-transfected COS cell media and GPI-PLD purified from serum were incubated at 37° C. for 30 min with 100 μl of VSG cocktail consisting of 40 μM Tris-maleate, pH 7.0, 0.2: NP-40, and $3 \times 10^4$ cpm $^3$H-labelled VSG. The reaction were terminated with the addition of 0.5 ml butanol and spiked with 25 mg each of dimyristoyl phosphatidic acid (DMPA) and dimyristoyl glycerol (DMG). After phase separation by centrifugation, 0.35 ml of the upper butanol phases were evaporated to dryness and the reaction products resuspended in 20 μl of CHC13:MeOH (1:1, v/v) and spotted onto a silica gel 60F254 plate (Merck), along with DMPA and DMG standards. The plate was run in a solvent system consisting of CHCl 3:pyridine:70% formic acid (50:30:7, v/v/v). After development for a distance of 10 cm, the plate was air dried overnight and the standards visualized with iodine. Zones of 0.5 cm were scraped, eluted with 150 ml CHCl 3:MeOH:-butanol (1:1:1, v/v/v), and counted in a scintillation fluorimeter. O ... O mock-transfected cell media; , pBJ1682-transfected cell media; .., purified serum GPI-PLD.

FIG. (9a–9J) Nucleotide sequence and deduced amino acid sequence of the human liver Glycosyl-Phosphatidylinositol specific-Phospholipase D.

FIG. (10A–10D) The Alignment of amino acid sequence of the human and bovine liver GPI-PLD mature protein.

FIG. (11A–11C) Nucleotide sequence and deduced amino acid sequence of the human pancreatic Glycosyl Phosphatidyl Inositol Specific-Phospholipase D.

Figure 12:
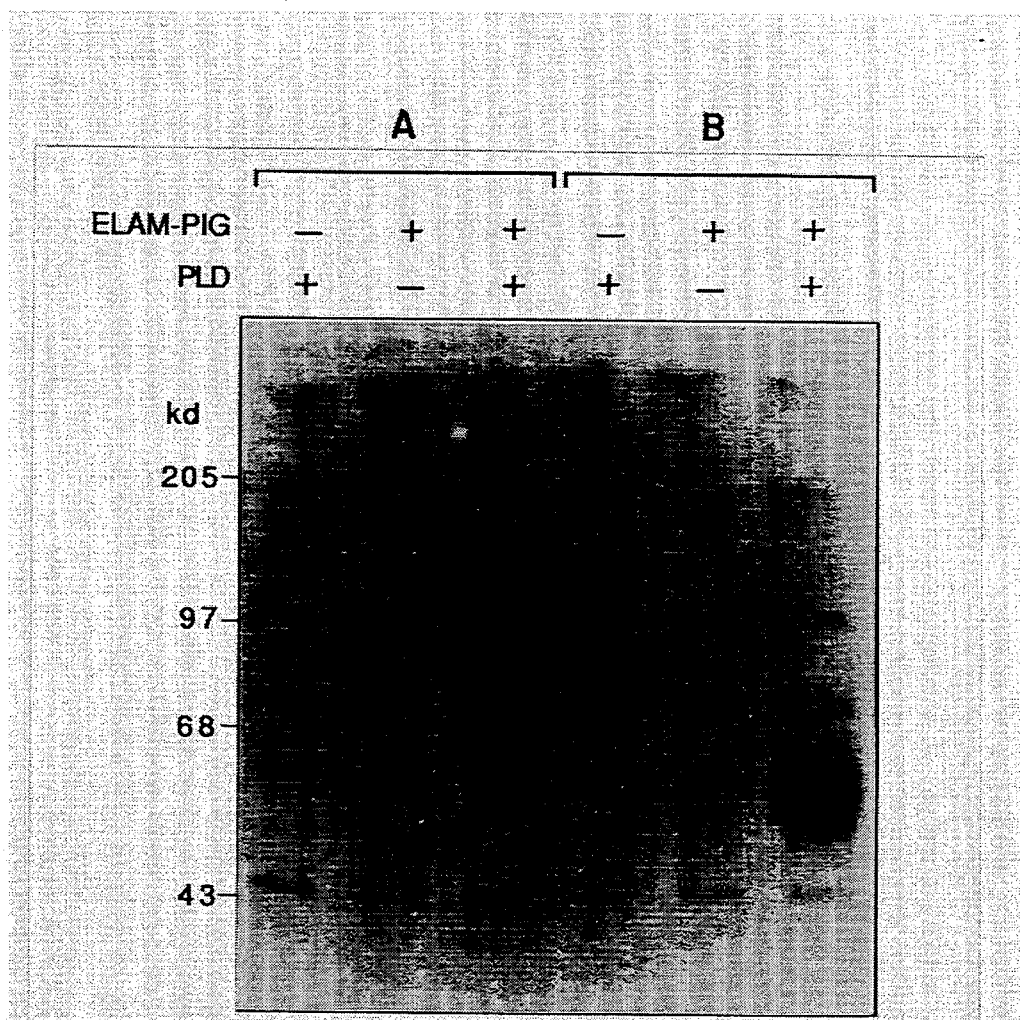

FIG. 12. SDS PAGE showing the expression of ELAM-1GPI (Column A) and ELAM-1-2-GPI (Column B) with PLD and without PLD.

Figure 13:
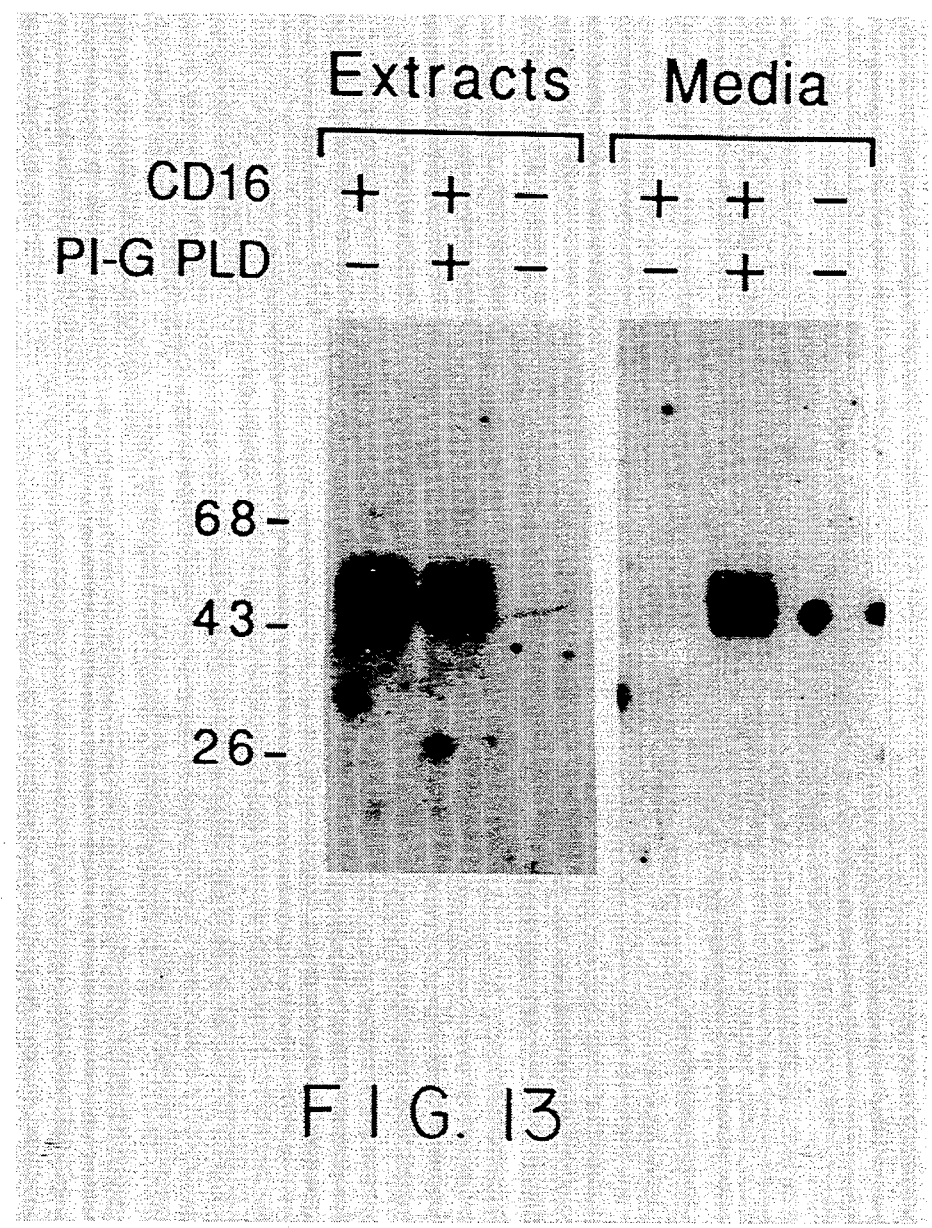

FIG. 13 Release of CD16 from COS cells transfected with CD16 and GPI PLD. COS cells were transfected with CD16 in the absence or presence of GPI PLD, labeled with $^3$H-ethanolamine, and the media or cell extracts immunoprecipitated with anti-CD16 mAb, 3G8. The precipitated proteins were fractionated by SDS-PAGE and radioactive proteins visualized by fluorography. The positions of the molecular weight markers (in kilodaltons) are marked.

Figure 14:
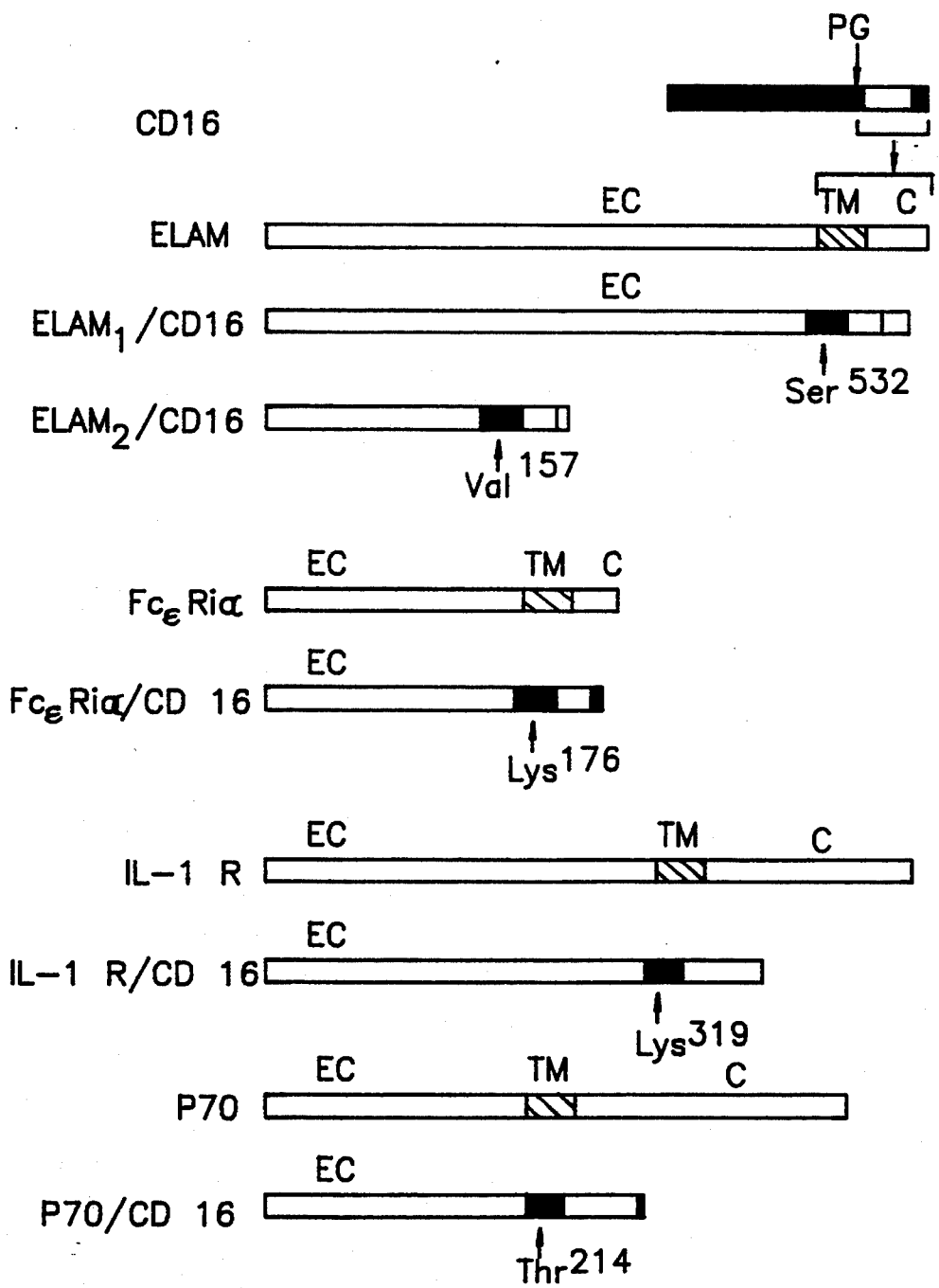

FIG. 14 Schematic representation of the chimeric gene constructs. DNA encoding the COOH-terminal 37 amino acids of CD16 (38–40) was spliced to the extracellular domain of various proteins. The COOH-terminal amino acid of each protein is shown. The lightly shaded box in CD16 represents the hydrophobic sequence. ELAM, endothelial leukocyte adhesion molecule-1; Fc$_\epsilon$RIα, high affinity IgE receptor alpha subunit; IL-1 R, interleukin-1 receptor; p70, β subunit of IL-2 receptor. EC, extracellular domain; TM, transmembrane domain; C, cytoplasmic domain.

FIG. 15 Cell surface immunofluorescence of GPI anchored forms of FcERIα. COS cells were transfected with DNA encoding FcERIα spliced to either the CD16 or PLAP GPI attachment signal sequence. The expression of the FcERIα was monitored with biotinylated human IgE followed by avidin FITC (52). The left panel is a phase contrast image, while the right panel is a fluorescent image.

Figure 16:
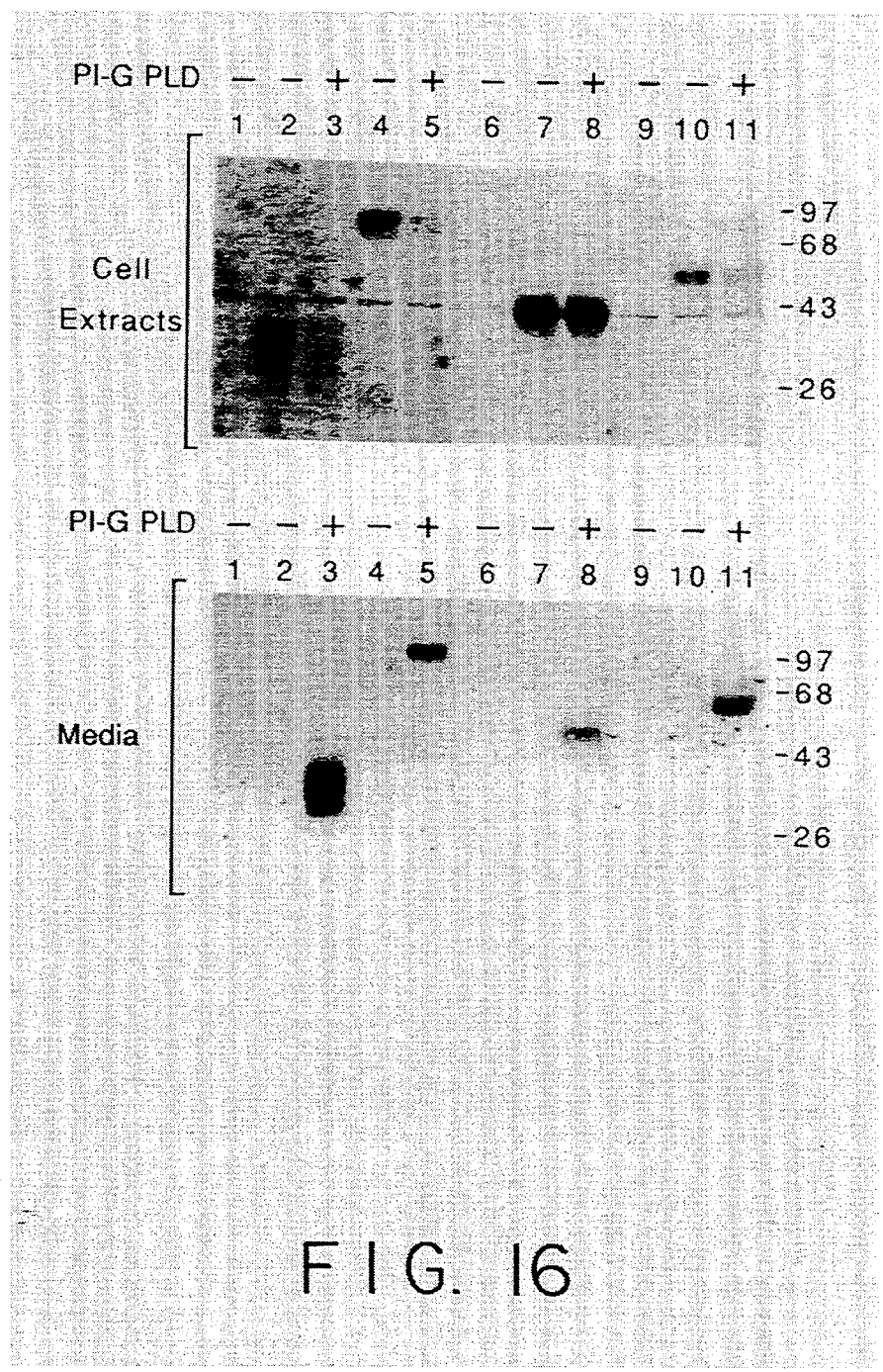

FIG. 16 Secretion of chimeric GPI anchored proteins in the presence of GPI PLD. COS cells were transfected with DNA encoding GPI chimeric proteins, readiolabeled with $^3$H-ethanolamine and the resulting cell extracts or supernatants were immunoprecipitated with corresponding antibodies and analyzed by SDS-PAGE. Lanes 1, wild-type ELAM-1; lanes 2 and 3, ELAM$_2$/CD16; lanes 4 and 5, ELAM$_1$/CD16; lane 6, wild type human FcERIα; lanes 7 and 8, FCE-RIα/CD16; lane 9, secreted form of the human IL-1 R; lanes 10 and 11, IL-1 R/CD16.

Figure 17:
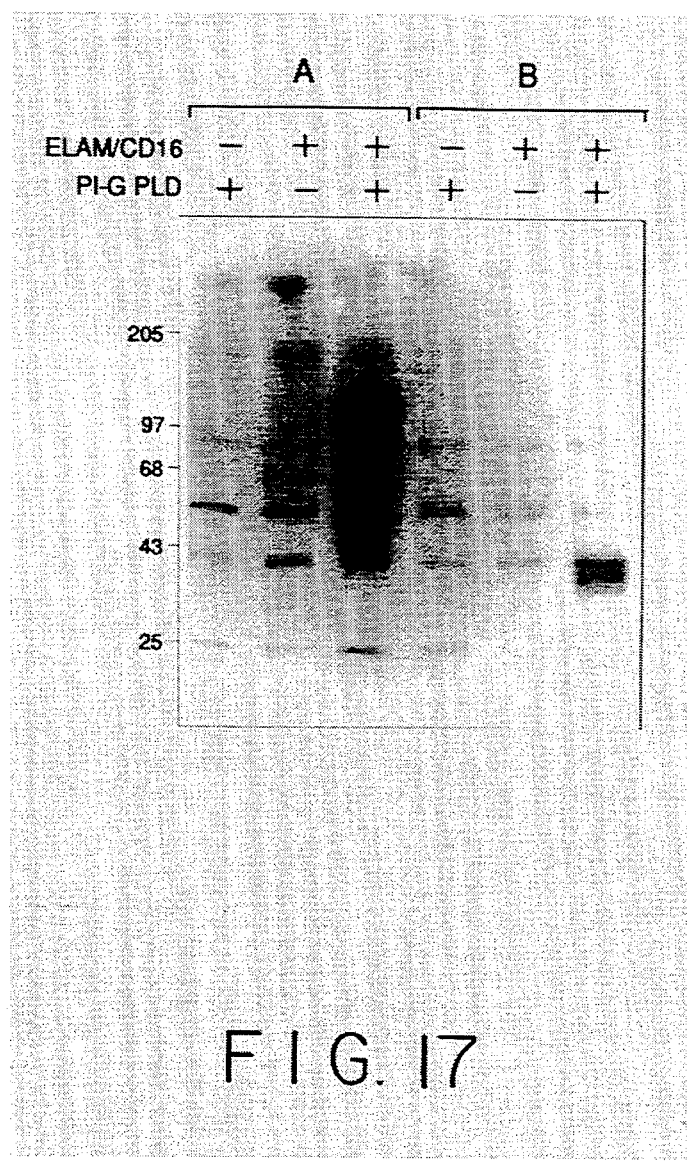

FIG. 17 GPI anchored ELAM is preferentially released in the presence of GPI PLD. COS cells were transfected with ELAM$_1$/CD16(A) or ELAM$_2$/CD16(B) in the presence or absence of GPI PLD and radiolabeled with $^{35}$S-cysteine. The supernatants were monitored for the secretion of ELAM by immunoprecipitation (as described above).

Figure 18:
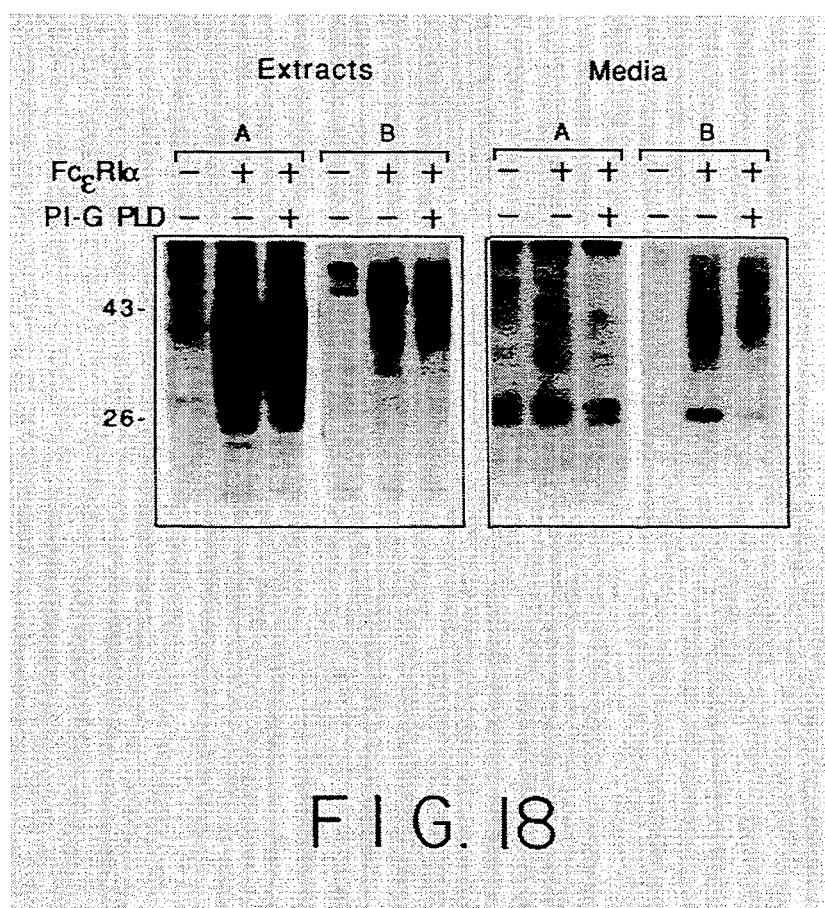

FIG. 18 GPI anchored FcERIα can be released in the presence or absence of GPI PLD. COS cells were transfected with FcERIα/CD16 with or without GPI PLD, and pulse labeled with $^{35}$S-cysteine for 2 hours (A) or followed by a 16 hour chase in the presence of unlabled cysteine (B). Cell extracts or supernatants were examined for the presence of FcERIα by immunoprecipitation with monoclonal antibodies. The precipitates were fractionated by SDS-PAGE and visualized by fluorography.

Figure 19:
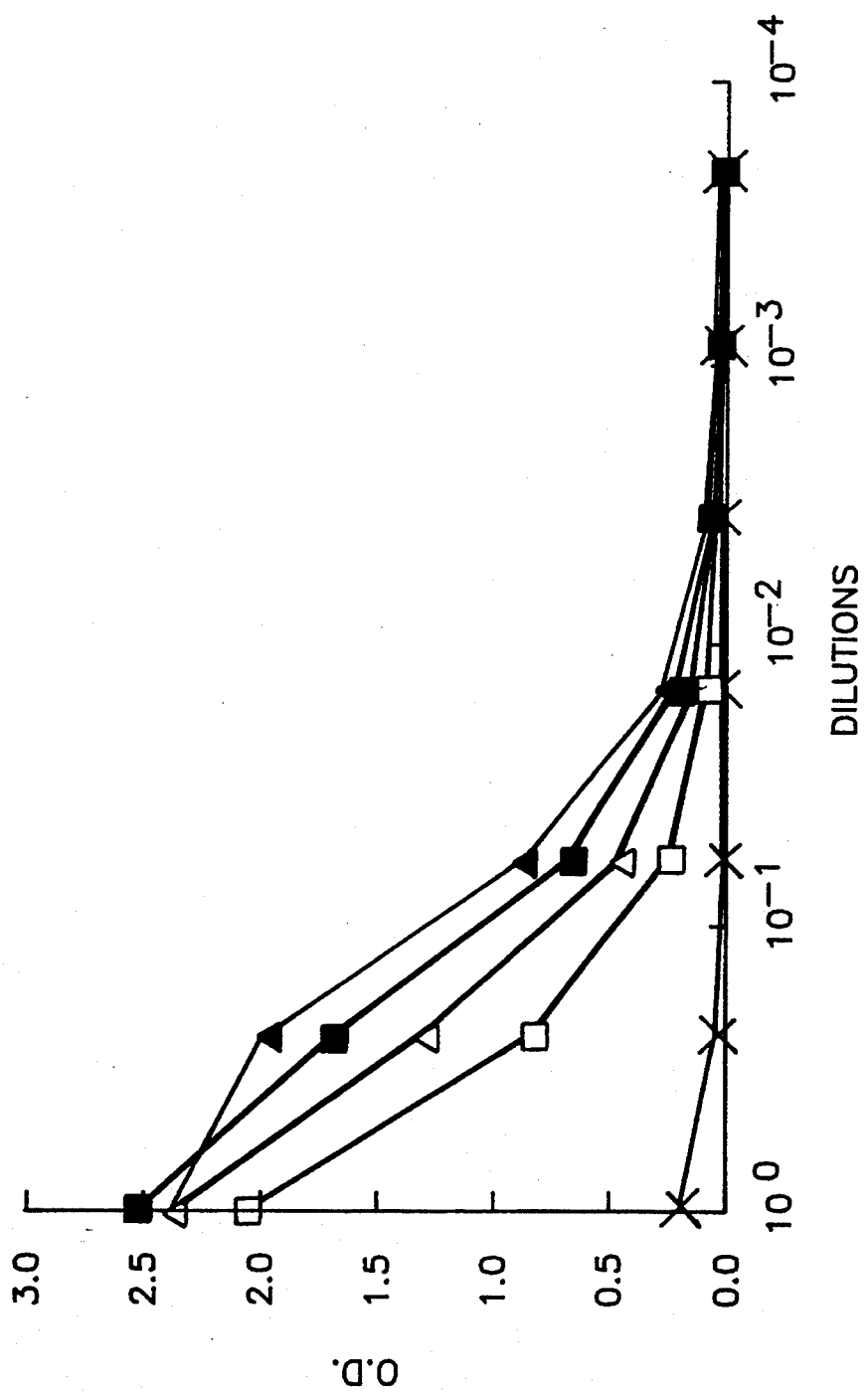

FIG. 19 Ligand binding activity of FcERIα released into the media of transfected COS cells in the absence or presence of GPI PLD. COS cells transfected with FcERIα/PLAP (triangles), FcERIα/CD16 (squares), either alone (open symbols) or with GPI PLD (filled symbols). 48 hours after transfection, media was harvested and assayed for the presence of IgE binding activity in a solid phase immunoabsorbent receptor binding assay (M. Nettleton and J. Kochan, manuscript in preparation). The supernants were diluted to measure the amount of FcERIα as determined by the optical density at 650 nm. A transmembrane form of the FcERIα subunit (52) (X . . . X) was used as a control.

DETAILED DESCRIPTION OF THE INVENTION

Figure 1:
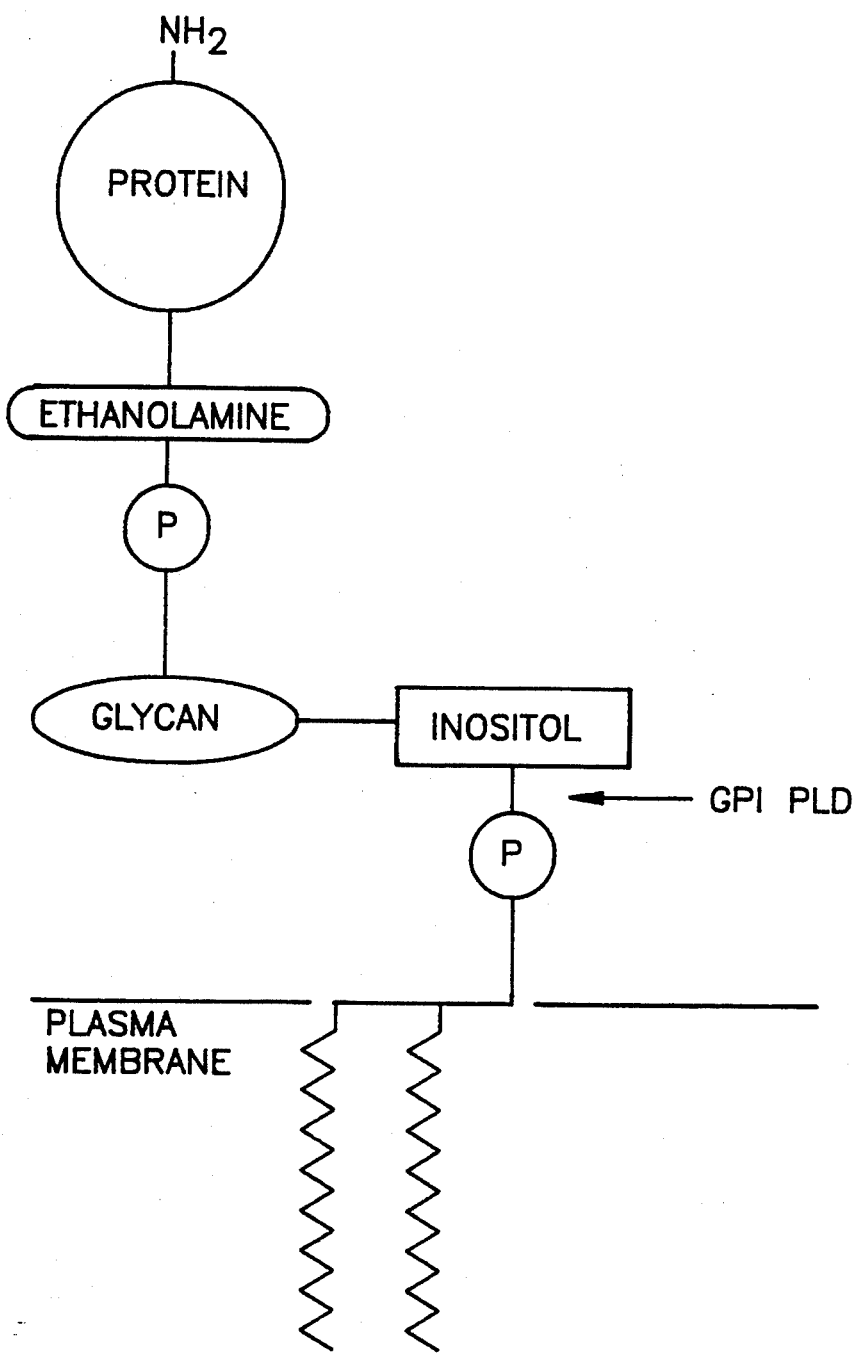
FIG. 1. A Model of a GPI anchor structure. The COOH-terminal amino acid of the protein is linked to an ethanolamine residue which in turn is linked via a phosphodiester bond to a complex glycan moiety. The site of GPI-PLD hydrolysis is marked.

The present invention involves glycosyl-phosphatidylinositol specific phospholipase D (GPI-PLD) or biologically active fragments thereof substantially free from other proteins. This enzyme selectively hydrolyzes the inositol-phosphate linkage of glycosyl-phosphatidylinositol(GPI)-anchored proteins, GPI lipids and related molecules. See FIG. 1. It is therefore possible to attach to any protein which is targeted for isolation a sequence which directs the attachment of the protein to a GPI anchor. When the protein is expressed in a cell which is also able to express GPI-PLD, the protein is secreted directly into the cell's medium from which it can be easily and coveniently isolated.

The DNA sequence and deduced amino acid sequence of bovine liver GPI-PLD is shown in FIG. 5; the DNA sequence and deduced amino acid sequence of human liver GPI-PLD is shown in FIG. 9; and FIG. 11 shows the DNA sequence and the deduced amino acid sequence of human pancreatic GPI-PLD. Using conventional methods of recombinant DNA technology, (see for example Maniatis et al., "Molecular Cloning—A Laboratory Manual". Cold Spring Harbor Laboratory. 1982) expression vectors encoding recombinant GPI-PLD can be constructed. Upon introduction of these expression vectors into a prokaryotic or eukaryotic host, recombinant GPI-PLD is synthesized.

The invention is also directed to mutations of GPI-PLD or biologically active fragments thereof which substantially retain the biological activity of natural GPI-PLD, an isolated nucleotide sequence encoding the mutant GPI-PLD or a biologically active fragment thereof, vectors containing the isolated nucleotide sequence encoding the mutant GPI-PLD or biologically active fragment thereof and cells transformed by a vector containing the isolated nucleotide sequence encoding the mutant GPI-PLD or a biologically active fragment thereof. These mutants can be produced by known methods such as site-specific mutagenesis of the DNA sequence and insertion of the mutant DNA construct into an expression vector and introduction of the expression vector into a suitable prokaryotic or eukaryotic host to produce a mutated form of GPI-PLD. A mutated form of GPI-PLD can also produced by means of enzymatic cleavage of the GPI-PLD protein and solid phase synthesis. The mutated form of the protein can then be assayed for its ability to exhibit PLD activity by assays herein described.

Also contemplated are antibodies specific to GPI-PLD substantially free from other proteins. A method for producing a secretable protein from a eukaryotic cell is claimed. Secretable proteins are produced by splicing the DNA sequence encoding the protein of interest together with a DNA sequence encoding a peptide which signals the attachment of a glycosyl-phosphatidylinositol anchor (GPI-anchor) onto the protein. An example of such a C-terminal GPI signal peptide which signal for the attachment of a GPI-anchor onto a protein is the C terminal 37 amino acids of CD16, namely:

Ser Thr Ile Ser Ser Phe Ser Pro Pro Gly Tyr Gln Val Ser Phe
21
Cys Leu Val Met Val Leu Leu Phe Ala Val Asp Thr Gly Leu
37
Tyr Phe Ser Val Lys Thr Asn Ile.

The DNA sequence encoding the C-terminal GPI signal peptide is spliced onto the DNA sequence encoding the functional domain of the proteins forming the protein-GPI-anchor construct. Preferably, the sequence is spliced to the 3' end of the DNA sequence so that it will be located at the C terminal of the protein. The protein-GPI-anchor hybrid construct is then co-transfected into a eukaryotic cell such as a COS cell with a gene encoding a GPI-PLD such that both the protein-GPI anchor signal peptide hybrid construct and the GPI-PLD gene are expressed. A GPI anchor is attached to the protein forming a GPI-anchor protein; GPI-PLD enzymes cleaves the anchor and the protein is secreted from the cell. Examples of proteins which could be produced and secreted in this way are CD4, ELAM-1, cytokine receptors such as p70 of the IL-2 receptor, and members of the integrin and selectin families to name just a few.

A process for cleaving proteins which are anchored to a cell by means of a glycosyl phosphatidyl inositol anchor comprising administering to a cell culture in which the cell is growing GPI-PLD in combination with a suitable detergent such as CHAPS or NONIDET P40 is disclosed.

A synthetic nucleotide sequence is claimed which is capable of causing expression of a protein connected to a glycosyl-phosphatidylinositol (GPI) anchor molecule, which sequence comprises nucleotides encoding glycosyl-phosphatidylinositol-specific phospholipase D (GPI-PLD), and nucleotides encoding the protein to be expressed linked to nucleotides encoding a C-terminal signal peptide which directs the attachment of a glycosyl-phosphatidylinositol anchor molecule to the protein to be expressed. The sequence so constructed will cause such expression in any host cell capable of producing a GPI anchor.

Many eukaryotic cells express the anchor, among them mammalian cells, yeast cells, and insect cells (3). Various means are known in the art for finding cells which produce the anchor. For example, one can determine whether a cell produces the GPI anchor by metabolically labelling cells with radioactive ethanolamine and analyzing the incorporation of radioactive ethanolamine by fluorography. Specific host cells useful in this invention include CHO cells, COS cells, HeLa cells, yeast cells, SF9 cells, and RBL-2H3 cells. However, any appropriate anchor-producing host cell may be used. Cells derived from liver or pancreas tissue are particular examples.

The nucleotide sequence is constructed by methods well known in the art of recombinant DNA technology, methods which are described in the Examples. GPI-PLD is described above. Nucleotide sequences of bovine and human GPI-PLD are provided in FIGS. 5, 9 and 11, and can be obtained from pancreatic or liver cells as described in the Examples, or can simply be synthesized in a DNA synthesizer based on the sequences provided.

Any protein is contemplated as a target protein to be built into this hybrid gene for secretion from a host cell. Proteins for use in this invention include for example selected members of the families of immunoglobulin and cytokine receptors, integrins, and selectins. Specific proteins include CD11A, CD11B, CD4, P- and L-selectin, ELAM-1, FcERIα, IL-1 receptor and p70 of the IL-2 receptor. T-cell receptors, including α, β, γ, or, δ subunits, and MHC class II proteins, including α, or β subunits, are also included. Nucleotide sequences encoding any protein may be obtained by well-known methods, for use in constructing the nucleotide sequence.

The C-terminal signal peptide which is a part of the construct causes the GPI anchor, which is produced by the host cell, to be attached to the target protein. Such a sequence may be isolated from the C-terminal region of any gene encoding a GPI-anchored protein by methods well known in the art. Also, examples of sequences themselves are known in the art and may be synthesized. A nucleotide sequence for a C-terminal signal peptide is provided in Example 6. This or homologous sequences may be used in this invention. In particular, the C-terminal signal peptides from the placental alkaline phosphatase gene (PLAP) or the human low affinity Ig G receptor (CD16) may be used. Combining the nucleotide sequences of GPI-PLD, a target protein, and a C-terminal signal peptide into a single sequence as claimed may be accomplished by DNA synthesis, since the component sequences are known or provided herein, or by recombinant methods using well-known techniques.

This invention also includes a vector capable of causing expression of a protein connected to a glycosyl-phosphatidylinositol anchor molecule, which vector contains a nucleotide sequence encoding glycosyl-phodphatidyl-inositol-specific phospholipase D, and a nucleotide sequence encoding the protein to be expressed linked to a nucleotide sequence encoding a C-terminal signal peptide which directs the attachment of a glycosyl-phosphatidylinositol anchor molecule to the protein to be expressed. Any known vector may be used in this invention. The nucleotide sequences are obtained as described above, and are inserted into the vector by well-known recombinant DNA methods. Contemplated vectors include plasmids, viruses, phagemids, cosmids, and other vectors known in the art. Vectors designed for expressing proteins in prokaryotic, and eukaryotic, e.g., mammalian, yeast, and insect cells are included. Particular examples of vectors are pBC12B1 and pRcCmV.

This invention includes isolated genes which encode the protein glycosyl-phosphatidylinositol-specific phospholipase D and have the nucleotide sequence depicted in FIGS. 5, 9, or 11. Isolation of these genes is described in the Examples. The sequence of these genes, provided herein, can be produced by well-known methods such as DNA synthesis. FIG. 5 depicts the sequence of bovine liver GPI-PLD. FIG. 9 depicts the sequence of human liver GPI-PLD, and FIG. 11 depicts the sequence of human pancreatic GPI-PLD.

This invention further includes a host cell capable of producing glycosyl-phosphatidylinositol anchor molecules which contains a nucleotide sequence encoding glycosyl-phosphatidylinositol-specific phospholipase D, and a vector containing a nucleotide sequence encoding a protein to be expressed linked to a nucleotide sequence encoding a C-terminal signal peptide which directs the attachment of a glycosyl-phosphatidylinositol anchor molecule to the protein to be expressed. As discussed above, any host cell is acceptable, and any expression vector suitable for said host cell. Insertion of a vector into a host cell is well-known in the art. Methods include transfection, transformation, electroporation, protoplast fusion, and other well-known methods. The host cell as described contains a gene encoding GPI-PLD, and a protein of choice which has been engineered as described above and in the Examples to have a C-terminal signal peptide. Therefore the cell will express the protein and the C-terminal signal peptide will direct the attachment of a GPI anchor to the protein. The cell will also express GPI-PLD, which will hydrolyze the GPI anchor, thus causing the protein to be secreted into the surrounding medium. An example of a host cell is a host cell which contains a single nucleotide sequence in a encoding all three components (GPI-PLD, the protein for secretion, and the C-terminal signal peptide). This system will also operate to secrete a protein of choice when the host cell contains a vector having a nucleotide sequence encoding GPI-PLD and a second vector having a nucleotide sequence encoding the protein of choice engineered to have a C-terminal signal peptide. Therefore, this invention includes a host cell capable of producing glycosyl-phosphatidylinositol anchor molecules which host cell contains both a first vector comprising a nucleotide sequence encoding glycosyl-phosphatidylinositol-specific phospholipase D, and a second vector comprising a nucleotide sequence encoding the protein to be expressed linked to a nucleotide sequence encoding a C-terminal signal peptide which directs the attachment of a glycosyl-phosphatidylinositol anchor molecule to the protein to be expressed.

Finally, this invention includes a process for obtaining a protein which comprises providing a host cell capable of producing glycosyl-phsophatidylinositol anchor molecules, inserting into said host cell a nucleotide sequence encoding glycosyl-phosphatidylinositol-specific phospholipase D, and a nucleotide sequence encoding the protein to be obtained linked to a nucleotide sequence encoding a C-terminal signal peptide which directs the attachment of a glycosyl-phsophatidylinositol anchor molecule to said protein, and incubating said host cell in medium to cause expression of said protein, whereby said protein is obtained in the medium.

Methods for isolating proteins from medium are well known in the art and are illustrated in the Examples.

Initial Purification of GPI-PLD by an Eight-step Scheme

In the present application the following abbreviations are used: GPI, glycosyl-phosphatidylinositol (also known as phosphatidylinositolglycan (PI-G)); PLD, phospholipase D; PI, phosphatidylinositol; VSG, variant surface glycoprotein; CHAPS, (3-[(3-cholamidopropyl)dimethylammonio] 1-propanesulfonate; PEG, polyethylene glycol; BSA, bovine serum albumin; EGTA, ethylenebis(oxyethylenenitrilo)tetraacetic acid; SDS, sodium dodecyl surfate; PAGE, polyacrylamide gel electrophoresis; HP(or FP)LC, high performance (or fast protein) liquid chromatography; PTH, phenylthio-hydantoin; ELISA, enzyme-linked immunosorbent assay; HRP, horse radish peroxidase.

The teachings of all of the references cited herein are hereby incorporated by reference.

An eight-step protocol for the purification of GPI-PLD from bovine serum was developed. In this procedure, the bulk of serum albumin and some other contaminating proteins were removed by PEG precipitation. The supernatant was then chromatographed on Q Sepharose (anion exchange) followed by S-300 gel filtration chromatography. GPI-PLD activity eluted in the broad second protein peak with a molecular weight of >250 kDa. This broad elution of activity suggests that GPI-PLD in serum may form a complex with other serum proteins.

GPI-PLD was further purified by wheat germ lectin-Sepharose and hydroxyapatite chromatography. At this stage, GPI-PLD was about 10% pure as judged by SDS-PAGE using procedures described by Laemmli (18). The final stages of purification consisted of Zn-chelate chromatography, Mono Q-HPLC and Superose 12-HPLC. When hydroxyapatite-purified material was chromatographed on Zn-chelate, two GPI-PLD activity peaks were observed. The first activity peak (pool 1) eluted in the wash fractions, separated from the majority of contaminating proteins and had the higher specific activity. This pool contained a major protein band on SDS-PAGE with an apparent molecular weight of ~100 kDa in addition to other minor protein bands. The second activity peak (pool 2) eluted with 10 mM histidine and contained two major protein bands with molecular weights of ~100 and ~180 kDa and several minor components on SDS-PAGE.

Figure 2:
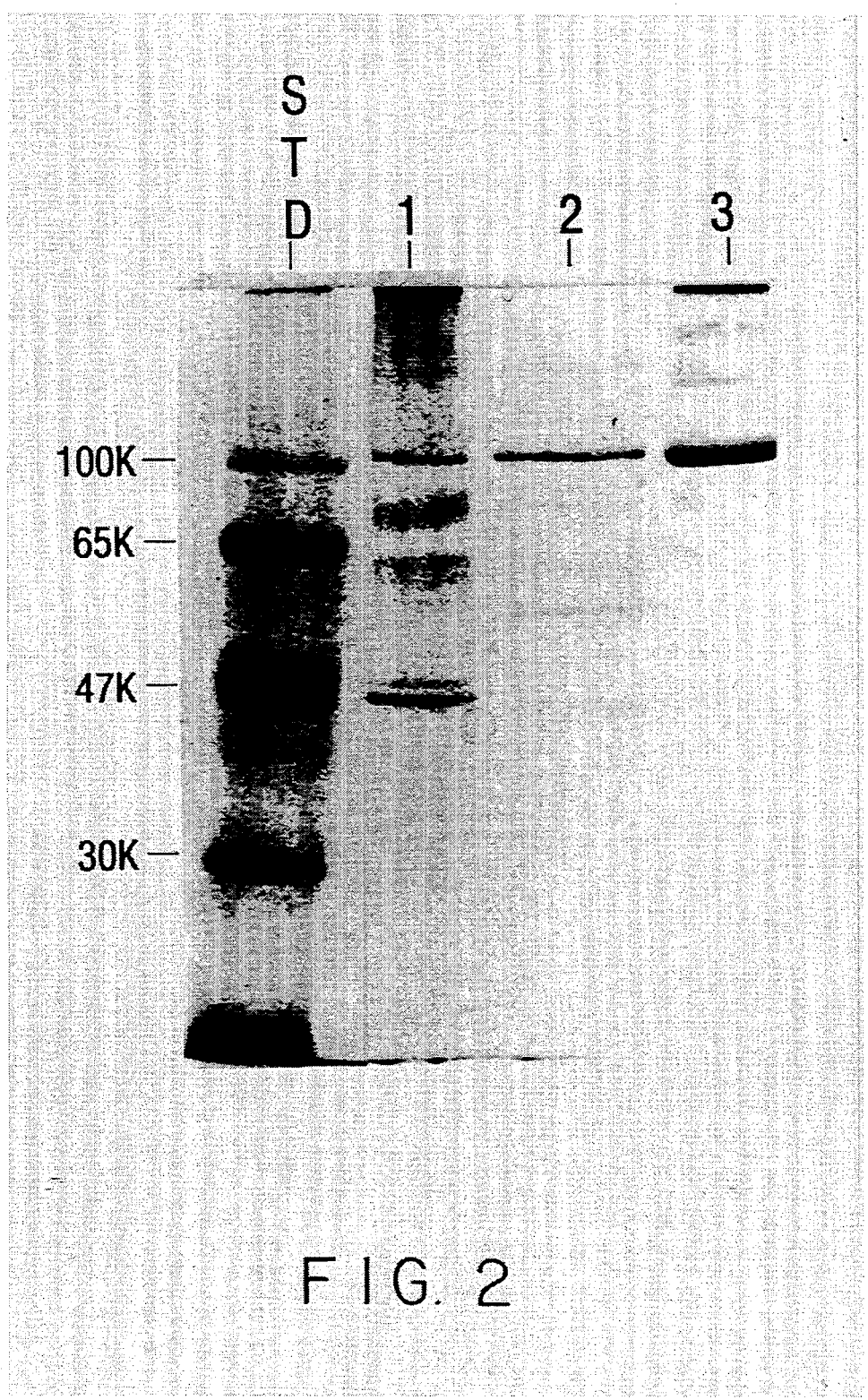
FIG. 2. SDS-PAGE of Samples Purified from Hydroxyapatite and Zn-chelate Matrix Chromatographies. Samples (1–3 μg) were run on 10% polyacrylamide gels (18) under reducing conditions and were visualized by Coomassie Blue staining. Protein standards (prestained) were from Bethesda Research Labs. Lane 1: hydroxyapatite flow-through pool (~3 μg); lane 2: Zn-chelate pool 1 (~1 μg); lane 3: Zn-chelate pool 2 (~3 μg).

The two pools of activity from Zn-chelate chromatography were separately further purified by Mono Q-HPLC. Zn-chelate pool 1 eluted as a single activity peak at 0.2M NaCl on Mono Q-HPLC, corresponding to a single band of molecular weight ~100 kDa on SDS-PAGE as shown in FIG. 2. lane 2. In contrast, Zn-chelate pool 2 resolved into two peaks of activity at 0.2M and 0.3M NaCl on Mono Q-HPLC. Both peaks contained a major protein band of ~100 kDa and another band corresponding to ~180 kDa on SDS-PAGE as shown in FIG. 2 lane 3.

When material eluted in Zn-chelate pool 1 was analyzed by Superose 12-HPLC, the elution profile showed that the GPI-PLD eluted as a single peak with an apparent molecular weight of about 200 kDa as determined by molecular weight markers (Bio-Rad's Gel Filtration Standards), indicating that the enzyme exists as a dimer. However, when material in peak 2 of Zn-chelate pool 2 was analyzed by Superose 12-HPLC, three activity peaks were observed. Actual fractions were analyzed by SDS-PAGE and the results showed that the majority of GPI-PLD eluted in fractions corresponding to the region with molecular weights higher than 200 kDa suggesting that GPI-PLD eluted as higher molecular weight aggregates. The higher molecular weight aggregates (peak 1) exhibited higher specific activity toward VSG (~$2.3 \times 10^4$ U/mg) than alkaline phosphatase ($1.0 \times 10^3$ U/mg) as substrate.

Table 1 summarizes the purification of GPI-PLD from 2.5 liters of bovine serum utilizing the protocol described above, excluding the Superose 12-HPLC step. Dimer GPI-PLD purified from Zn-chelate, pool 1, showed the highest specific activity ($6.3 \times 10^5$ and $4.5 \times 10^5$ U/mg against alkaline phosphatase and VSG, respectively). This represents a ~2,250 fold purification and an overall recovery of about 0.5%.

Production of Monoclonal Antibodies against GPI-PLD

Using a mixture of dimeric and aggregated GPI-PLD as immunogen, polyclonal antisera in mice against GPI-PLD were produced. All three immunized mice produced antibodies against the immunogen as determined by ELISA analysis. GPI-PLD activities were completely inactivated by antisera when purified or partially purified protein was used. When partially purified material was analyzed by immunoblotting, the 100-kDa protein was reactive with the antisera.

To further confirm that the 100-kDa protein is GPI-PLD, monoclonal antibodies against the enzyme were produced. Since serum contains GPI-PLD, hybridomas were grown in serum-free medium after fusion. Hybridoma supernatants were analyzed by ELISA. Clones secreting high levels of IgG antibodies were further screened in an immunodepletion assay against GPI-PLD activity. Twenty-four clones were obtained after subcloning. To further analyze the immunoprecipitated product, $^{125}$I-labelled immunogen was used in an immunodepletion assay and the products analyzed by SDS-PAGE. The results show that the antibodies in the hybridoma supernatants selectively precipitated the GPI-PLD activity and the 100-kDa protein.

The cells from ELISA-positive and immunodepletion-positive wells were subcloned. Twenty four clones were isolated and expanded as ascites tumors in BALB/cByJ mice. The monoclonal antibodies were purified and screened for their reactivity with the 100-kDa protein by immunoblotting analysis. Nineteen showed strong reactivity. The immunoreactivity of the 100-kDa protein was dependent on antibody concentration and was saturated by excess antibody. Preabsorption of antibody with excess purified GPI-PLD diminished immunoreactivity (lane 5). The purified antibodies were also screened for direct inhibition of GPI-PLD activity in solution. None of them inhibited GPI-PLD.

Purification of GPI-PLD by Immunoaffinity Chromatography

Figure 3:
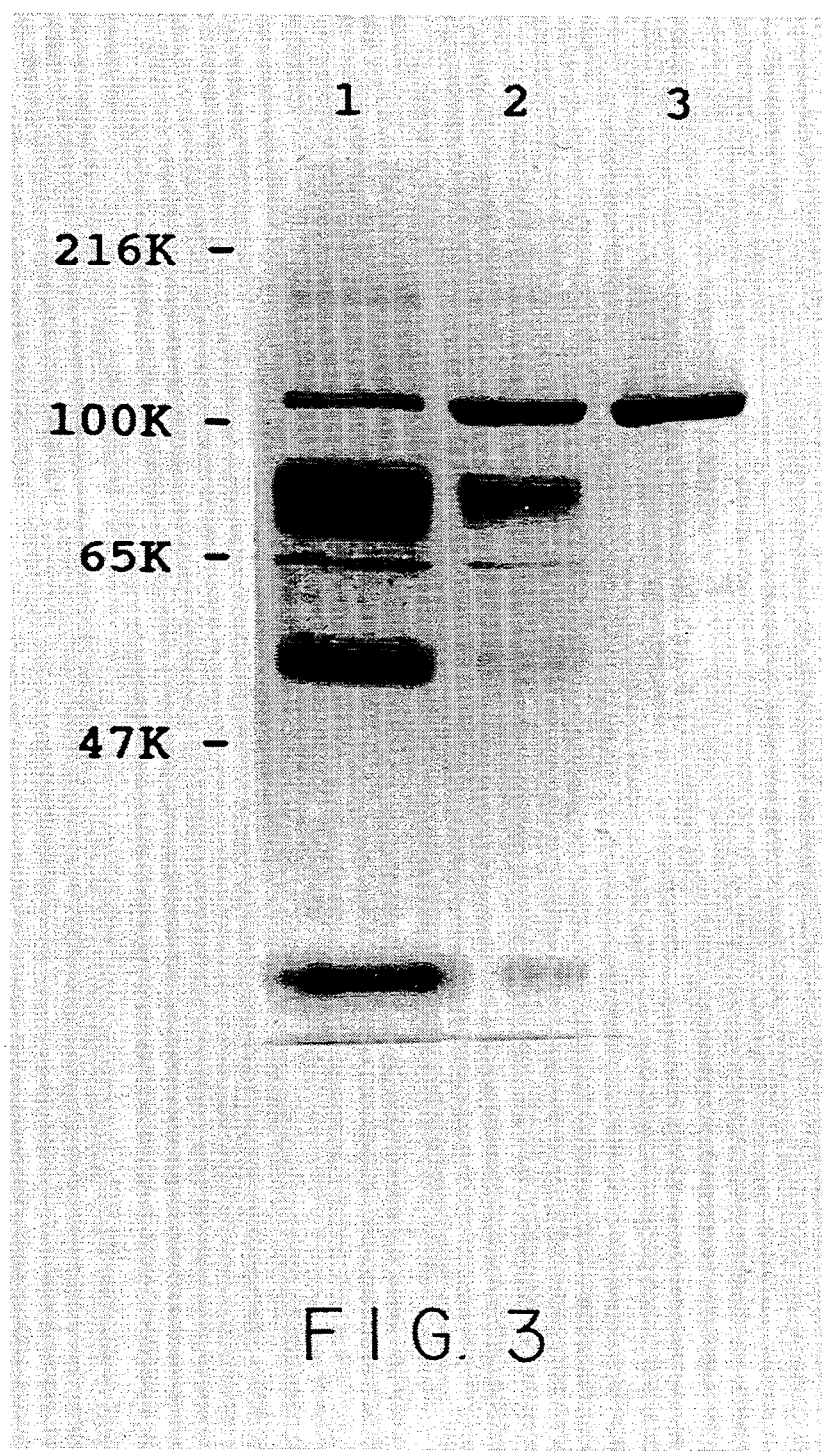
FIG. 3. SDS-PAGE of Samples Purified by the Immunoaffinity Chromatography Procedure. Samples were run on 8.5% acrylamide gels under reducing conditions and were visualized by Coomassie Blue staining. Lane 1: immunoaffinity-eluate, ~10 μg; late 2: lectin Sepharose-eluate, ~5.0 μg; lane 3: Mono Q-FPLC pool ~2.5 μg.
Figure 4:
FIG. 4. Restriction Map and sequencing strategy of the spliced inserts from Clones pBJ1549 and pBJ1644. The bovine liver GPI-PLD cDNA inserts from the two lambda gt11 clones were subcloned into pGEM4Z (Promega Biotec, Madison, Wis.) and both strands sequenced using Sequenase enzyme (U.S. Biochemical Corp., Cleveland, Ohio). Arrows with closed and open circles represent sequences determined from SP6/T7 promoter primers of smaller subclones and sequences determined from synthetic oligonucleotide primers, respectively. The positions of the translation start and stop codon are marked. Clones pBJ1549 and pBJ1644 extended from nucleotides 1–1577 and 1438–2578, respectively. A, AccI; b, BamHI; H, HindIII; K, kpnI; N, NcoI; P, PstI; S, SacI; V, PvuII.

It was determined which of the monoclonal antibodies would be most suitable for immunoaffinity chromatography. Antibodies with different affinities to GPI-PLD on ELISAs were separately coupled to CNBr-activated Sepharose. Crude bovine serum was loaded onto immunoaffinity columns and GPI-PLD activity was eluted by different reagents. The results showed that when weak affinity antibodies were used, bound GPI-PLD could be eluted with 3M MgCl$_2$ with about 60% recovery of activity. However, when high affinity antibodies were used, only a very small amount of GPI-PLD could be eluted with 3M MgCl$_2$. Although SDS-PAGE analysis indicated that most of the remaining bound protein could be eluted with 0.1M glycine-HCl buffer (pH 2.8), enzymatic activity was lost. A weak affinity antibody was therefore chosen for immunoaffinity purification. The eluate from immunoaffinity chromatography gave a specific activity of about $9.75 \times 10^3$ U/mg, representing a 123 fold purification (see Table 2). Based upon this specific activity (assuming that the purified enzyme has a specific activity of $4.5 \times 10^5$ U/mg) and SDS-PAGE analysis a GPI-PLD purity of about 2% was calculated. See FIG. 3 lane 1.

Since the immunoaffinity-purified GPI-PLD could not be stably stored in 3M MgCl$_2$, it was immediately diluted 6 fold with Buffer C (see Example 1) supplemented with 2.5 mM each CaCl$_2$ and zinc acetate. Calcium and zinc ions in the dilution buffer seemed to stabilize the enzyme activity, consistent with previous observations that the enzyme activity is dependent on calcium and zinc ions, but not Mg$^{+2}$. GPI-PLD in the diluted sample was then further purified on wheat germ lectin Sepharose. As shown in Table 2, a 10 fold purification was achieved with lectin Sepharose chromatography. On SDS-PAGE (FIG. 3, lane 2), the lectin Sepharose-eluate showed that although the major contaminating proteins were still in the sample, there was an enrichment of the 100-kDa GPI-PLD. GPI-PLD was further purified by Mono Q-FPLC. The elution profile showed that most of the activity eluted in a peak at 0.2M NaCl, although a very small amount of activity also eluted at 0.3M NaCl. When the samples were analyzed by SDS-PAGE, the major activity peak showed a single band with a molecular weight of 100 kDa. See FIG. 3 lane 3. Samples in the minor activity peak also showed a very small amount (less than 10% of the total GPI-PLD recovered from the column) of 100-kDa protein together with other contaminating proteins. When the purified GPI-PLD was analyzed by Superose 12-HPLC, it eluted as a single peak with an apparent molecular weight of 200 kDa.

Table 2 summarizes the purification of GPI-PLD from 200 ml of bovine serum by the immunoaffinity chromatography protocol as described above. The specific activity of purified GPI-PLD from the immunoaffinity procedure was about the same as that obtained by the eight-step procedure. However, the overall recovery (26%) was much higher.

Characterization of GPI-PLD

The products of [$^3$H]myristate labelled VSG hydrolysis by the purified GPI-PLD were analyzed by thin layer chromatography on silica gel using two different solvent systems (chloroform:pyridine:70% formic acid, 50:30:7 or chloroform:methanol:glacial acetic acid:-H$_2$O, 50:30:8:4). The $^3$H-labelled product co-migrated with a dimyristyl phosphatidic acid standard. Other potential phospholipase products such as myristic acid and 1,2-dimyristoyl glycerol were not detectable (i.e. less than 5% of recovered radioactivity). This result was obtained with both the dimeric form and the higher molecular weight aggregates.

The sensitivity of the enzyme activities to EGTA and 1,10-phenanthroline was studied Table 3 shows that all enzyme activities are inhibited by EGTA and 1,10-phenanthroline, indicating that all forms of GPI-PLD share a metal ion requirement. To further study the physical properties of dimer and aggregates of GPI-PLD, purified GPI-PLD was labeled with $^{125}$I and the different forms of GPI-PLD were separated by Superose 12-HPLC. Each form of GPI-PLD was then rerun on Superose 12-HPLC. The results showed that the elution positions of these forms remained unchanged, indicating that the forms are not in equilibrium with each other.

The 100-kDa proteins in dimer and larger aggregated forms were isolated by preparative SDS-PAGE and subjected to amino-terminal sequence analyses. The results show that all forms of GPI-PLD share the same amino terminal sequence (H$_2$N-X-G-I-S-T-(H)-I-E-I-G-X-(R)-A-L-E-F-L--). A search within the GenBank and NBRF data bases using the computer programs TFASTA and SEARCH showed no strong sequence homology to that of any other known protein.

The primary structural relationships between these forms of GPI-PLD were also studied by comparing their tryptic peptide maps. Both samples were digested with trypsin, and cleavage products were separated by reverse phase HPLC on a $C_8$ column. The tryptic peptide maps are almost identical, indicating that the two forms of GPI-PLD represent either the same protein or are structurally very similar.

The tryptic peptides were further analyzed by protein microsequence analysis. Table 4 summarizes sequences derived from nine peak fractions.

The present invention is further illustrated by the following Examples, which are not intended to limit the invention.

EXAMPLE 1

Purification and Characterization of PLD

Materials—Bovine serum was from Pel-Freez Biologicals. PEG-500C was from Polyscience Inc. Hydroxyapatite Ultrogel was from IBF Biotechnics. CNBr-activated Sepharose, Q Sepharose, wheat germ lectin-Sepharose and Sephacryl S-300 were from Pharmacia. IODO-BEADS, and immobilized (Fractogel TSK HW-65F) iminodiacetic acid was from Pierce. CHAPS, (4-(2-hydroxyethyl)-1-piperazine ethanesulfonic acid (HEPES), phenyl methyl sulfonyl floride (PMSF), Triton X-114 and 100, Nonidet P40 and goat anti-mouse IgG agarose were from Sigma. HRP conjugated goat F(ab')$_2$ anti-mouse IgG was from TAGO. Female Balb/c and Balb/cByJ mice were from Charles River Labs and Jackson Labs, respectively.

Solutions—Buffer A: 10 mM HEPES, pH 7.0, 0.15M NaCl, 0.1 mM $MgCl_2$ and 0.01 mM zinc acetate; Buffer B: 50 mM Tris, pH 7.5, 0.1M NaCl, 0.5 mM PMSF and 0.02% $NAN_3$; Buffer C: 50 mM Tris, pH 7.5, 0.1M NaCl, 0.6% CHAPS and 0.02% $NaN_3$.

GPI-PLD assays—For the eight-step purification of GPI-PLD, the enzyme activity was assayed as described in Low and Prasad(6) and Huang, Li and Low(9) and using GPI-anchored placental alkaline phosphatase as substrate. Typically, the alkaline phosphatase substrate (0.05 ml containing 1 vol of alkaline phosphatase, purified as described in Malik and Low (5) 2 vol of 1% NP-40 and 2 vol of 0.2M Tris-maleate, pH 7) was incubated with aliquots of samples in a total volume of 0.2 ml for 30 min at 37° C. The mixture was then diluted with 0.8 ml of ice-cold Buffer A. An aliquot (0.05 ml) was removed and mixed with 0.2 ml of Buffer A and 0.25 ml of 2% precondensed Triton X-114. After sampling a 0.1 ml aliquot for assay of total alkaline phosphatase activity, the mixture was incubated at 37° C. for 10 min, centrifuged immediately at room temperature for 2 min and a 0.1 ml aliquot of the upper (aqueous) phase sampled. Alkaline phosphatase activity was determined. Anchor degradation was measured by comparing the activity in the upper phase (i.e., the degraded form) with that in the total mixture before phase separation. One unit is arbitrarily defined as the amount of enzyme hydrolyzing 1% of the alkaline phosphatase per min under the assay conditions described.

For the purification of GPI-PLD by immunoaffinity chromatography VSG biosynthetically labelled with [$^3$H]myristate was used as substrate. This was prepared by a modified procedure described in Huang, Li, and Low, (9) of a published method described in Hereld, Krakow, Bangs, Hart, and Englund, (10). Typically, *T. brucei* (MItat 117 or 118) were prepared from infected rats, labelled with -[$^3$H]myristic acid in vitro and the $^3$H-labelled VSG was isolated. [$^3$H]Myristate-labelled VSG (4,000–5,000 cpm, 2 μg) was mixed with 0.02 ml of 0.2M Tris maleate, pH 7.0, 0.02 ml of 1% NP-40 and 0.06 ml of $H_2O$. The substrate (0.1 ml) was then incubated with the GPI-PLD sample (0.1 ml) for 30 min at 37° C. The reaction was stopped by the addition of 0.5 ml of butanol that had been saturated with 1M ammonium hydroxide. After vortexing, the phases were separated by centrifugation at 1,500×g for 3 min. The upper (butanol) phase (0.35 ml) was withdrawn, mixed with 4 ml of scintillation fluid, and counted. One unit of GPI-PLD activity using VSG as a substrate is arbitrarily defined as the amount of enzyme hydrolyzing 1% of the [$^3$H]myristate-labelled VSG per min.

To determine the substrate specificity of GPI-PLD, the products of [$^3$H]myristate-labelled VSG hydrolysis by purified GPI-PLD were analyzed by thin-layer chromatography as described by Low, and Prasad, (6). Hydrolysis of [$^3$H]choline-labelled phosphatidylcholine and [$^3$H]inositol-labelled PI was determined by substituting them for VSG in the incubation mixture described above. Water soluble radioactivity released from the phospholipids was determined as described by Low, Stiernberg, Waneck, Flavell, and Kincade, (11).

Purification of GPI-PLD by the Eight-step Procedure

Bovine serum (2.5 l) was thawed at 4° C. in the presence of 0.5 mM PMSF and 0.02% $NaN_3$. With stirring at 4° C., PEG-5000 was gradually added to a final concentration of 9%. The mixture was stirred for an additional hour and centrifuged at 10,000×g for 25 min. The supernatant was collected and diluted with an equal volume of Buffer B. All subsequent purification steps were performed at 4° C. except where noted.

The diluted supernatant was loaded at a flow rate of 30 ml/min onto a Q Sepharose column (9×10 cm) equilibrated in Buffer B. After washing with the equilibration buffer, GPI-PLD activity was eluted with a linear gradient of 0.1–1.0M NaCl in 4 l of 50 mM Tris, pH 7.5, 0.02% $NaN_3$ and 0.5 mM PMSF. Fractions containing activity were pooled and concentrated by YM-10 (Amicon) membrane filtration to approximately 200 ml. The concentrate was loaded at a flow rate of 3.8 ml/min onto two (10×53 cm) S-300 columns in Buffer B, linked in tandem. The activity fractions were pooled, and NaCl and CHAPS were added to final concentrations of 0.2M and 0.6%, respectively, to minimize protein aggregation. Half of the sample was loaded (flow rate: 17 ml/hr) onto a 40 ml (2.5 cm diameter) wheat germ lectin column equilibrated in 50 mM Tris, pH 7.5, 0.2M NaCl, 0.02% $NaN_3$ and 0.6% CHAPS. After washing, the GPI-PLD activity was eluted with equilibrium buffer containing 0.3M N-acetylglucosamine. The eluates from two runs were combined and concentrated to 10 ml. Nine volumes of 5 mM $NaPO_4$, pH 6.8, 0.4% CHAPS and 0.02% $NaN_3$ were added and the sample was loaded at room temperature (flow rate: 3 ml/min) onto a 4.2×22 cm column of hydroxyapatite Ultrogel in 5 mM $NaPO_4$, pH 6.8, 0.6% CHAPS and 0.02% $NaN_3$. GPI-PLD activity was collected in the wash fractions, and the contaminating proteins were eluted with 0.5M $NaPO_4$, pH 6.8, 0.6% CHAPS, and 0.02% $NaN_3$.

GPI-PLD active fractions from hydroxyapatite agarose chromatography were pooled, concentrated by YM-10 membrane filtration to 21 ml, and the pH adjusted with the addition of a 20-fold dilution of 1M Tris HCl, pH 7.5. The sample was loaded onto a column (1.5×5.0 cm) of iminodiacetic acid on Fractogel TSK HW-65F chelated with zinc and equilibrated in Buffer C. The first peak of activity was collected in 10-15 bed volumes of wash with equilibration buffer and a sharper second peak of activity was eluted with 10 mM histidine in equilibration buffer.

The two Zn-chelate pools of activity were concentrated individually by YM-10 membrane filtration. Each sample (5 ml) was injected onto a Mono Q (HR5/5, Pharmacia) column equilibrated in Buffer C (without NAN3) at room temperature. GPI-PLD activities were eluted at a flow rate of 1 ml/min with a gradient of 0.1-0.19M NaCl in 50 mM Tris, pH 7.5, and 0.6% CHAPS in 6 min, followed by isocratic elution at 0.19M NaCl for 5 min and a gradient of 0.19-0.4M NaCl in 14 min. Under these conditions, the first Zn-chelate pool eluted as one activity peak at 0.2M NaCl whereas the second Zn-chelate pool resolved into two peaks of activity at 0.2M and 0.3M NaCl.

GPI-PLD active fractions from Mono Q-HPLC were pooled, concentrated, and each sample (0.4 ml) injected onto a Superose 12-HPLC (HR 10/30, Pharmacia) column equilibrated in Buffer C. Proteins were eluted at a flow rate of 0.3 ml/min and 0.5 ml fractions were collected.

Purification of GPI-PLD by Immunoaffinity Chromatography

Monoclonal antibody PLD 216.1 was coupled to CNBr-activated Sepharose at a final concentration of 1 mg/ml resin. Bovine serum (200 ml was centrifuged at 16,000×g for 20 min, and the supernatant diluted with 1.2 liters of Buffer B plus 0.5% NP-40. After filtering through a 0.22 μm membrane (Nalgene filter unit), the sample was loaded onto an immunoaffinity column (20 ml, 2.5×4 cm) at a flow rate of 30 ml/hr. The column was then washed with 400 ml of Buffer C and GPI-PLD eluted with 3M MgCl$^2$ in Buffer C. Active fractions were pooled (100 ml, 40 mg) and immediately diluted with 6 volumes of Buffer C plus 2.5 mM each CaCl$_2$ and zinc acetate. The sample was then loaded at a flow rate of 30 ml/hr onto a 20 ml (2.5 cm diameter) wheat germ lectin Sepharose column in 50 mM Tris, pH 7.5, 0.2M NaCl, 0.6% CHAPS, 0.02% NaN3 plus 2.5 mM each CaCl$_2$ and zinc acetate (equilibrium buffer). After the column was washed, the sample was eluted with 0.3M N-acetylglucosamine in equilibrium buffer.

The pool (60 ml, 2.5 mg) of wheat germ lectin Sepharose-eluate was concentrated by YM-10 membrane filtration to about 15 ml and diluted with an equal volume of 50 mM Tris, pH 7.5, and 0.6% CHAPS. The sample was then loaded onto Mono Q-FPLC equilibrated in Buffer C (without NaN3) at room temperature. GPI-PLD was eluted at a flow rate of 1 ml/min with a gradient of NaCl as described above.

Protein Determinations—Protein concentration during purification was monitored by absorbance at 280 nm. In addition, the protein concentration of purified preparations was determined by the method of Bradford (12) using Bio-Rad's protein assay reagent. One mg/ml of purified GPI-PLD corresponded to one optical density unit at 280 nm.

Tryptic Peptide Mapping—The 100 kDa proteins in peaks 1 and 2 from Mono Q-HPLC were isolated by preparative SDS-PAGE. Proteins were recovered by electroelution in 67 mM N-ethylmorpholine acetate, pH 8.6, and 0.05% SDS as described in Hunkapillar, Lujan, Ostrader, and Hood (13). After electroelution, proteins (100 μg) were reduced with 10 mM dithiothreitol for 2 h at 37° C. and alkylated with 20 mM iodoacetic acid for 30 min at room temperature in the dark. Additional 10 mM dithiothreitol was added to the mixture to stop the reaction. Samples were lyophilized and proteins precipitated with acetone:acetic acid: triethylamine:water (85:5:5:5, by vol.). The precipitated proteins were washed twice with ice-cold acetone, dried and resuspended in 0.3 ml 0.1M NH$_4$HCO$_3$, pH 8.0, and 0.5 mM CaCl$_2$. Samples were digested for 16 hr at 37° C. with TPCK-treated trypsin (Cooper Biomedical, 6 μg total). The trypsin was added in three equal aliquots: the first at time zero, the second after 4 h, and the third after a 12 h incubation. Samples were acidified with formic acid to 15% and subjected to reverse phase HPLC on a C$_8$ column (Phase Separation Inc., 0.2×15 cm). Peptides were eluted (flow rate: 0.2 ml/min) with a gradient of acetonitrile (0-70%) in 0.1% trifluoroacetic acid.

Protein Sequencing—Sequence analysis was performed using an Applied Biosystems (ABI, Foster City, Calif.) gas sequencer model 470A. PTH amino acids were identified "on line" with an ABI model 120A PTH analyzer using a reverse-phase C-18 column (2.1×220 mm, ABI).

Preparation of Monoclonal Antibodies against GPI-PLD—A female BALB/c mouse was immunized intraperitoneally with a mixture of two forms of mono Q-HPLC-purified GPI-PLD (60 μg protein) mixed 1:1 with Freund's complete adjuvant. Four weeks later, the mouse was boosted intraperitoneally with the same amount of immunogen in Freund's incomplete adjuvant. A test bleed was taken a week later and antiserum was checked by ELISA and by direct assay for neutralization of GPI-PLD activities.

Three days before fusion, the mouse was further boosted with 60 μg of immunogen by intravenous injection into the tail vein. Spleen cells from the mouse were fused with the myeloma cell line PAI-0 using procedures described by Thomas, Reik, Ryan, and Levin (14). Ten days after fusion, the cells were weaned into serum-free media (HL-1, Ventrex Laboratories) and 40 h later, supernatants were analyzed by ELISA for IgG production against the immunogen. ELISA positive cultures were expanded in serum-free media. Hybridomas exhibiting poor growth in serum-free media were grown in 0.5% horse serum. Under such conditions, endogenous horse serum GPI-PLD did not interfere with either the ELISA or immunodepletion assay. The established hybridoma cells were then grown as ascites tumors in pristane-primed BALB/cByJ mice. Anti-GPI-PLD monoclonal antibodies were purified from ascites fluids by caprylic acid and ammonium sulfate precipitation as described by Reik, Maines, Ryan, Levin, Bandiera, and Thomas (15).

ELISA—Non-competitive ELISA assays were run against mouse antiserum and culture supernatants as described by Thomas, Reik, Ryan, and Levin (14). Either immunogen or partially purified (wheat germ lectin- or Zn-chelate matrix-) GPI-PLD was coated onto 96-well polystyrene microtest plates. Binding of antibodies to GPI-PLD-coated plates was detected using HRP-conjugated second antibody and an appropriate chromogen as described by Thomas, Reik, Ryan, and Levin (14).

Immunodepletion assay—Hybridoma supernatants were screened for their abilities to immunoprecipitate GPI-PLD activity. Culture supernatants (0.5 ml) were incubated with 50 µl of a 50% suspension of goat anti-mouse IgG-agarose for 1 h at 37° C. BSA (0.5 mg) was added as a carrier protein. The beads were washed twice with 1 ml Buffer A plus 0.5% NP-40 and incubated with 40 µl wheat germ lectin-purified GPI-PLD diluted with Buffer A plus 1 mg/ml BSA. After 1 h at 37° C., the beads were removed by centrifugation at 1,500×g for 0.5 min, and the supernatants were analyzed for GPI-PLD activity using either alkaline phosphatase or $^3$H-VSG as substrate.

Immunoblotting—Immunoblotting was carried out as previously described by Towbin, Staehlin, and Gordon (16). Antibodies (mouse antiserum or purified monoclonal antibodies) and second antibodies (HRP-goat F(ab')$_2$ anti-mouse IgG) were diluted in phosphate-buffered saline, 1% BSA, 5% normal goat serum, and 0.05% Tween 20. After several washes, peroxidase activity was detected with 4-chloro-1-napthol and hydrogen peroxide, as previously described by Nielsen, Manchester, Towbin, Gordon and Thomas (17).

Immunoprecipitation—Dimer GPI-PLD was iodinated with $^{125}$I using IODO-BEADS. Free $^{125}$I was removed with a desalting column (Econo-Pac 10DG, Bio-Rad). Hybridoma supernatants (0.25 ml each) were incubated with goat anti-mouse IgG-agarose beads (0.05 ml of 50% slurry) at 37° C. for 1.5 hr. BSA (0.2 mg) was added to each sample as a carrier protein during incubation. The mixtures were then centrifuged at 1,500×g for 0.5 min, and the beads were incubated overnight at 4° C. with $^{125}$I-labelled GPI-PLD (3.5×10$^5$ cpm) in 0.25 ml of 50 mM Tris, pH 7.5, 0.1M NaCl, 0.5% NP-40, and 1 mg/ml BSA. The beads were removed by centrifugation and washed three times (0.8 ml each) with 50 mM Tris, pH 7.5, 0.1M NaCl, and 0.5% NP-40. SDS-PAGE reducing sample buffer (40 µl) was added to the beads and aliquots (20 µl) were analyzed by SDS-PAGE. After electrophoresis, the gels were dried under vacuum and autoradiographed.

A GPI-specific phospholipase D was obtained from bovine serum by two different methods. The enzyme was initially purified by an eight-step procedure. Using the purified enzyme as immunogen, a panel of monoclonal antibodies against GPI-PLD were generated. Purified GPI-PLD from bovine serum was also accomplished by a simple procedure involving immunoaffinity chromatography, wheat germ lectin Sepharose and Mono Q-FPLC. The enzyme purified by the latter procedure is present as a dimer as analyzed by gel filtration-HPLC. However, the material purified by the eight-step procedure contains a mixture of dimer and higher molecular weight aggregates. These forms of GPI-PLD can be separated by Mono Q- and gel filtration-HPLC. On SDS-PAGE, the purified enzyme shows a single protein band with a molecular weight of 100 kDa. On native isoelectric focusing gels, each form of GPI-PLD exhibits a common pI of about 5.6. Using VSG or alkaline phosphatase as substrate, the dimer exhibits a much higher specific activity than the higher aggregates.

When the 100-kDa protein and its tryptic peptides were subjected to amino acid sequencing analyses, the sequence data revealed no strong homologies to those of other known proteins except for the homology of two tryptic peptide sequences to each other and to the $Ca^{+2}$ binding domains of calcium binding proteins. The discovery of two potential metal binding sequences is interesting in view of the data reported here and elsewhere that the enzyme activity is sensitive to the addition of divalent metal ion chelators, such as EGTA and 1,10-phenanthroline.

From Table 2, we estimate that GPI-PLD exists in bovine serum at a concentration of approximately 7 µg per ml. This is a high circulating level of enzyme, indicating a significant physiological role.

TABLE 1

Purification of GPI-PLD by the Eight-step Procedure

| Step | Protein (mg) | PLD Activity[a] (U) | Sp. Activity (U/A$_{280}$) | Purification Factor |
|---|---|---|---|---|
| Bovine Serum | 146,855 | 4.1 × 10$^7$ | 2.8 × 10$^2$ | 1 |
| PEG Sup. | 67,365 | 3.1 × 10$^7$ | 4.6 × 10$^2$ | 1.6 |
| Fast Q | 3,686 | 7.5 × 10$^6$ | 2.0 × 10$^3$ | 7.1 |
| S-300 | 920 | 3.1 × 10$^6$ | 3.4 × 10$^3$ | 12.1 |
| Wheat Germ Lectin | 106 | 2.2 × 10$^6$ | 2.1 × 10$^4$ | 75 |
| Hydroxyapatite | 14 | 1.6 × 10$^6$ | 1.1 × 10$^5$ | 392 |
| Zn-chelate, pool 1 | 0.8 | 4.1 × 10$^5$ | 5.1 × 10$^5$ | 1,821 |
| pool 2 | 2.5 | 3.0 × 10$^5$ | 1.2 × 10$^5$ | (b) |
| Mono Q (Zn-chelate Pool 1) peak 1 | 0.1 | 6.3 × 10$^4$ | 6.3 × 10$^5$ | 2,250 |
| Mono Q (Zn-chelate Pool 2) | | | | |
| peak 1 | 0.28 | 4.0 × 10$^4$ | 1.5 × 10$^5$ | (b) |
| peak 2 | 0.4 | 1.5 × 10$^4$ | 3.8 × 10$^4$ | (b) |

[a]GPI-PLD activity was determined using alkaline phosphatase as substrate.
[b]Since portions of GPI-PLD in the sample were present as aggregates with low specific activities, the degree of purification could not be determined accurately.

TABLE 2

Purification of GPI-PLD by Immunoaffinity Chromatography

| Step | Protein (mg) | PLD Activity[a] (U) | Sp. Activity (U/A$_{280}$) | Purification Factor |
|---|---|---|---|---|
| Bovine Serum | 8,333 | 6.6 × 10$^5$ | 7.9 × 10$^{(b)}$ | 1 |
| Immunoaffinity | 40 | 3.9 × 10$^5$ | 9.8 × 10$^3$ | 123 |
| Wheat Germ Lectin | 2.5 | 2.4 × 10$^5$ | 1.0 × 10$^5$ | 1,266 |
| Mono Q-FPLC | 0.4 | 1.7 × 10$^5$ | 4.3 × 10$^5$ | 5,443[c] |

[a]GPI-PLD activity was determined using [$^3$H]-VSG as a substrate.
[b]The specific activity of GPI-PLD in bovine serum shown in this Table is somewhat lower than that in Table 1 due to the variability in the commercially available material.
[c]The purification factor shown in this Table is higher than that in Table 1 due to the lower specific activity of the starting material.

TABLE 3

Inhibitor Sensitivity of Two Forms of GPI-PLD

| Enzyme | Inhibitor | Activity remaining (%) |
| --- | --- | --- |
| GPI-PLD (dimer) | None | 100 |
| | EGTA (1.5 mM) | 83 |
| | EGTA (5.0 mM) | 18 |
| | 1,10-phenanthroline (0.075 mM) | 26 |
| | 1,10-phenanthroline (0.5 mM) | 3 |
| GPI-PLD (aggregates) | None | 100 |
| | EGTA (1.5 mM) | 38 |
| | EGTA (5.0 mM) | 11 |
| | 1,10-phenanthroline (0.075 mM) | 44 |
| | 1,10-phenanthroline (0.5 mM) | 1.3 |

Mono Q-HPLC peaks 1 ($A_{280}$: 0.162) and 2 ($A_{280}$: 0.319) were diluted 400-fold with 10 mM HEPES, pH 7.0, and 0.15M NaCl. An aliquot (0.1 ml) was incubated with various amounts of inhibitors for 1 hr at 4° C. in a total volume of 0.11 ml. GPI-PLD activity was determined using VSG as substrate. Inhibitor concentrations refer to those present in the final incubation. Activities are expressed relative to those of controls.

TABLE 4

Sequences of Tryptic Peptides Generated from GPI-PLD

| Fragment | (pmol) | Sequence |
| --- | --- | --- |
| $T_{56}$ | (~50) | SPFLVEQFQEYFLGGLEDMAFXSTNI |
| $T_{50}$ | (~15) | SIXEMFIGSXQPLTHV |
| $T_{44}$ | (~75) | VYGYFPXIC(Q)SIFT |
| | (~20) | MVADVNXHX(L)GPE |
| $T_{38}$ | (~80) | LGXAMTSADLNQDGYGDLVVGAPG(Y)X(H)PG |
| $T_{37}$ | (~150) | FGSAVAVLDFNVDGVPDLAVGAPSVGS(E)(K) |
| $T_{35}$ | (~120) | ALEFLHLQDGSINYK |
| | (~20) | HQDAYQAGSVFPDSF |
| $T_{34}$ | (~100) | HQDAYQAGSVFPDSFYPSICER |
| | (~50) | VSFLTMTLHQGGSTR |
| $T_{20}$ | (~325) | AQYVLISPEAGSR |
| | (~205) | FGSSV(I)TVR |
| $T_{18}$[a] | (~110) | SNVTS (CPEEK) [FWYLP] R |

Tryptic fragments of the SDS-PAGE-purified 100-kDa protein were subjected to amino-terminal microsequence analysis on a gas phase sequencer. 'X' indicates positions in the sequence where PTH-amino acids were not identified. The numbers in parentheses indicate the estimated amount of peptide sequenced. The amino acids in parentheses indicate the most likely assignments.
[a]The two peptides in this fraction exist in equimolar amounts and the first six residues in the assigned sequences may be exchanged with each other at the corresponding positions.

EXAMPLE 2

Cloning and Expression of Bovine Glycosyl Phosphatidyl Inositol—Specific Phospholipase D Bovine liver cDNA libraries were screened with synthetic oligonucleotides corresponding to peptide sequences derived from purified bovine glycosyl phosphatidyl inositol-specific phospholipase D (GPI-PLD). Two overlapping clones were isolated that together predict the exact amino acid sequence of all eight tryptic fragments that had been sequenced. The DNA sequence of the two clones predicted a mature protein of 817 amino acids and an additional signal peptide of 23 amino acids. The deduced sequence contained eight potential N-linked glycosylation sites and at least four regions with sequence similarity to metal ion binding domains of members of the integrin family (19). These observations were consistant with the characterized GPI-PLD being 100 kd in size, glycosylated, and metal ion-dependent. The identification of the cloned cDNA was confirmed by two assays for biological activity. First, culture media and cell lysates of COS cells transfected with the gene showed phospholipase activity using $^3$H-labelled GPI-anchored variant surface glycoprotein (VSG) of the African trypanosome as substrate in an in vitro assay. Analysis of the products from the in vitro VSG assays by thin layer chromatography showed that phosphatidic acid was a reaction product confirming that the phospholipase activity was that of phospholipase D. Second, COS cells transfected with a gene encoding GPI-anchored placental alkaline phosphatase (PLAP) released significant amounts of PLAP into the media when co-transfected with the GPI-PLD clone but not when transfected alone. These results suggest that GPI-PLD may play a role in the regulation of cell surface expression of GPI-anchored proteins in vivo.

The amino acid sequence of eight tryptic fragments from bovine GPI-PLD was used to design a set of four degenerate oligonucleotide probes for the purpose of screening by DNA hybridization bovine DNA libraries. Because PLD activity had been detected in liver extracts, a liver cDNA library was initially screened. No positive clones were detected among the $5 \times 10^5$ clones screened. However, the screening of a bovine genomic library yielded one positive clone that hybridized to one of the four oligonucleotide probes. Partial DNA sequence analysis of this clone revealed an open reading frame that predicted exactly the sequence of the 22 amino acid tryptic fragment, T34. However, this coding sequence was in an exon that appeared to be only 79 bp in length. Instead of characterizing this genomic clone further, a second attempt at isolating a cDNA clone was made using two non-degenerate 30-mer oligonucleotides corresponding to the 79 bp exon sequence. In addition, a new bovine live cDNA library was constructed using random hexanucleotides to prime first strand synthesis. From $5 \times 10^5$ clones screened, two positive ones were isolated with the longer insert being 1.6 kb in length (clone pBJ1549). The complete sequence of the 1.6 kb insert was determined and shown to predict exactly the amino acid sequence of five of the eight tryptic fragments reported including (as expected) fragment T34 encoded by the genomic clone. Comparison of the deduced protein sequence to the N-terminal sequence of intact GPI-PLD revealed that the clone encoded the mature N-terminus of the protein ($Cys^1$ in FIG. 5). It is likely, then, that the initial translation product contains a 23 amino acid peptide.

Clone pBJ1549 was considered incomplete because 1) it encoded a protein of only 50 kd while a core protein of 80-100 kd was expected, 2) three of the eight tryptic sequences were not accounted for, and 3) an in-frame translation stop condon was not present. To isolate clones encoding the C-terminus, a liver cDNA library was screened with a nick-translated 400 bp fragment from the 3' end of pBJ1549. One clone was isolated that had a 1.1 kb insert (clone pBJ1644). Sequence analysis showed that the insert began at nucleotide 1450 of pBJ1549 and extended 1090 nucleotides in the direction of the C-terminus. The two clones had identical sequences in the 140 base region of overlap. The open reading frame identified in pBJ1549 continued in pBJ1644 until a stop codon at nucleotide 2557. The pBJ1644 insert encoded exactly the three tryptic fragments not encoded by pBJ1549. Together they encoded a 23 amino acid signal peptide and a 816 amino acid mature protein (90.2 kd) with eight possible N-linked glycosylation sites. These data indicated it was likely that these two clones combined contained the complete coding sequence for this protein.

Analysis of the deduced amino acid sequence revealed four regions of internal similarity (amino acids 379-402, 448-471, 511-534, and 716-739) that ranged from 21% to 54% identical (54% to 75% similar) to each other. A computer search in amino acid and nucleotide sequence databases revealed significant similarity of these repeats with the metal ion binding domains of the integrin alpha subunits. They share an aspartate-rich core sequence flanked by short conserved segments which are unique to the integrins. Apart from the absence of a glutamate residue, the core sequence DX(D/N)XDGXXD matches the EF-hand consensus motif characteristic of a number of $Ca^{+2}$ and $Mg^{+2}$ binding proteins such as calmodulin, troponin C, and parvalbuim. The observation that the gene reported here contains domains similar to metal ion binding domains of the integrins is consistent with the calcium requirements of GPI-PLD in enzymatic assays.

To express the cloned cDNAs and confirm that the encoded protein was GPI-PLD, the two inserts were first spliced together at the AccI site in their region of overlap and the resulting 2.6 kB cDNA ligated into the eukaryotic expression plasmid, pBC12BI (Cullen, Methods in Enzymol. 152:684-704 (1987)). The resulting plasmid, pBJ1682, was introduced into COS cells and expression confirmed by using a pool of monoclonal antibodies against the purified serum enzyme to perform 1) immunofluoresence of permeabilized cells, and 2) Western blot analysis. While mock-transfected cell medium and lysate showed no detectable immunoreactive proteins by Western blot (lanes 1 and 2), pBJ1682transfected cells produced an immunoreactive protein detectable in both the medium and the lysate of sizes consistent with that of a glycosylated 90 kD core protein (lanes 3 and 4). However, the protein detected in the lysate migrated slightly faster than the protein secreted into the medium which in turn migrated faster then purified serum GPI-PLD. To demonstrate that these differences in migration were not due to differences in the types of sample (e.g. lysate vs. medium), pBJ1682-transfected cell medium or lysates were mixed with an equal volume of mock-transfected cell lysate or medium, respectively, prior to loading on the gel. The nature of these differences in size (estimated to be as much as 10 kd between lysate and purified serum proteins) is under investigation and may provide an important clue as to how the active form of this enzyme differs from its inactive form (see below).

Culture media and cell lysates of the pBJ1682-transfected or mock-transfected COS cells were then prepared and incubated with $^3$H-labelled GPI-anchored variant surface glycoprotein (VSG) to test for phospholipase activity. As shown in FIG. 7A, significant amount of phospholipase activity was detected in the medium of DNA-transfected cells while only background levels of activity were detected in mock-transfected cells. After 46 hours in serum-free medium, the amount of phospholipase activity secreted reached 65 U/ml (approximately 0.15 µg/ml assuming that the COS cell secreted enzyme had the same specific activity as the purified bovine serum enzyme). FIG. 7B shows that from pBJ1682-transfected cells only a small amount of phospholipase activity was observed in the lysates compared to the media. These results indicated that the cloned gene did encode phospholipase enzyme and that most of the enzymatic activity was secreted from the cells.

Analysis of the reaction products of $^3$H-labelled VSG hydrolysis assays confirmed that the phospholipase activity in DNA-transfected cells was that of phospholipase D. See FIG. 8. The major $^3$H-labelled product resulting from hydrolysis by purified serum GPI-PLD or the conditioned media from transfected cells comigrated with dimyristoyl phosphatidic acid during thin-layer chromatography.

Transfected COS cell lysates and conditioned media were also examined for their specificites against non-GPI linked dipalmitoyl phosphatidylcholine substrate in the presence of ethanol. Neither PA nor phosphatidylethanol (a transphosphatidylation product of Phosphatidylcholine specific PLD in the presence of ethanol) were detected by thin layer chromatography confirmed gene was the GPI-specific form of PLD.

EXAMPLE 3

Transfection of COS Cell With a Gene Encoding GPI-Anchored Protein Alone and With A Gene Encoding GPI-PLD To test for in vivo phospholipase activity against a GPI-anchored substrate, COS cells were transfected with a gene encoding GPI-anchored placental alkaline phosphatase (PLAP) alone or co-transfected with pBJ1682. Cell media and lysates were assayed for alkaline phosphatase activity. When COS cells were transfected with the PLAP cDNA alone, the majority of PLAP activity was detected in the cell lysate. This was consistent with PLAP being a GPI-anchored protein. When COS cells were co-transfected with both PLAP and pBJ1682, the amount of PLAP secreted into the medium was much higher then that of cells transfected with PLAP cDNA alone. The PLAP activity in the lysate of co-transfected cells was slightly higher than that of cells transfected with PLAP only, suggesting that in cotransfected cells GPI-anchored PLAP was constantly being synthesized and released by phospholipase activity. This was also supported by the fact that the total PLAP activity detected in the medium and lysates of co-transfected cells was consistently much higher than that in cells transfected with PLAP alone. In COS cells transfected with pBJ1682 DNA alone, only background levels of endogenous PLAP were detected in the medium or lysates. These results demonstrated that the cloned phospholipase could greatly affect the cell-surface expression of a GPI-anchored protein.

To test whether the GPI-PLD secreted from COS cells would hydrolyze cell-surface GPI-anchored PLAP, media from pBJ1682-transfected cells was incubated with PLAP-transfected cells and aliquots of media were assayed for PLAP activity after 1, 3, 8 and 24 hours of incubation. No PLAP activity was detected even though the media were active in the VSG assay both before and after the 24 hour incubation period.

As an alternative means of determining whether GPI-anchored proteins were hydrolysed by GPI-PLD, the cell culture supernatants of co-transfected COS cells were examined by immunoprecipitation following labelling with $^3$H-ethanolamine. If GPI-anchored proteins were actually being hydrolyzed by GPI-PLD, then the hydrolytically derived products would be expected to maintain the $^3$H-ethanolamine moiety. This is in contrast to hydrolytic products derived by proteolysis, which would not contain this group. Both PLAP and CD16 can be released from GPI-PLD co-transfected cells in a form which still contains an ethanolamine residue. These results eliminate the possibility that the released proteins are proteolytically derived products, and demonstrate that at least two different GPI-anchored proteins can be released by GPI-PLD.

EXAMPLE 4

Molecular Cloning of the Human Liver Phospholipase D Gene

Tryptic peptide fragment sequences of a bovine GPI-PLD and DNA sequence from a partial bovine genomic clone were available. Using this information, a pair of oligonucleotides (#1s, #1a) were designed to search for a human source of PLD mRNA by the polymerase chain reaction. In liver, the presence of the message was detected by a 81-bp amplicon. Based on bovine cDNA sequences, primers were prepared (#5s, #4a) to amplify the 1.2 kb fragment corresponding to the 5' half of the phospholipase D transcript from human liver first-strand cDNA.

A partial human GPI-PLD cDNA clone was isolated by library screening. Human liver polyA+ mRNA was primed using oligo-dT and size selected. EcoRI-linkered cDNA was cloned into the lambda-ZAP II vector (Stratagene). This library of 2.5 million recombinants was screened unamplified in duplicate with the bovine cDNA (at low stringency) and the 1.2-kb human GPI-PLD amplicon (at high stringency). A positive clone was identified by both probes and the insert was sequenced. This partial cDNA clone (nucleotide 688-1247) encoded 186 amino acid residues (230-416).

Since the mature amino terminus of human GPI-PLD was found to be highly conserved with that of the bovine protein (11 amino acids identical of the first 12) and partial C-terminus sequence of a human pancreas PLD cDNA was available, two oligonucleotides (#5s, #9a) were made to amplify a 2.5-kb amplicon from human liver first-strand cDNA. The segment corresponds to sequence coding for the mature human phospholipase D gene product. The amplicon was cloned into the vector pRcCmV (Invitrogen) and pBC12BI-derived vectors for expression in mammalian cells.

The DNA sequence coding for the mature human GPI-PLD protein was obtained from two independently isolated clones of the 2.5 kb amplicon, the partial cDNA clone and the 1.2 kb amplicon (described above; see FIG. 9). The predicted peptide sequence is 817 amino acid and 82% identical to the bovine sequence.

To clone the signal peptide of human GPI-PLD, an oligonucleotide (#5RT) was designed to prime cDNA synthesis from liver polyA+ RNA. An adaptor-linker was ligated to the ends of the cDNA which was then subjected to two rounds of PCR using an adaptor primer and the oligonucleotides #5amp followed by #237. A 300 bp amplicon detected by #5s on a Southern blot was subcloned and the sequence of seven clones were determined. The Signal peptide of human liver GPI-PLD is 24 amino acids long and the sequence matched closely to that of the bovine GPI-PLD.* The human liver signal peptide was joined to the mature protein coding region via a HpaI site in the pRcCMV expression construct.

*(14 amino acids identical)

Material and Methods

Oligonucleotides

| #    | Sequence                        | nucleotide   | positions |
|------|---------------------------------|--------------|-----------|
| 1s:  | CTGTTACTTAGGCACCAGG             | bovine       | 85–103    |
| 1a:  | CTCTCTCACAGATGCTAGG             | bovine       | 144–162   |
| 5s:  | TGTGGCCTTTCGACACACATAGAAATAGG   | human        | 1–29      |
| 4a:  | ACGCGCCCCACGTGAATGCGGCCTGGGTG   | bovine       | 1150–1178 |
| 9a:  | TCAATCTGAGCCAAGGCTATAGAC        | human        | 2430–2453 |
| 5RT: | GAATCCTTGTTCAATG                | human liver  | 411–426   |
| 5amp | CTGCTACCATATGAGAAGTA            | human liver  | 388–369   |
| 237: | TATGCATCCTGGTCTTCT              | human liver  | 182–165   |

Polymerase Chain Reaction (PCR)

Plasmid or genomic DNA, single stranded cDNA, or lambda phage have been used as templates in PCRs. A 50 μl-reaction contains 10 mM Tris-HCl pH8.3 at 25° C., 1.5 mM MgCl$_2$, 50 mM KCl, 0.01% (w/v) gelatin, template DNA, a pair of oligonucleotide primers (50 pmol each), 2.5 units Taq DNA polymerase (Cetus-Perkin Elmer) and 200 uM of dATP, dCTP, dGTP, dTTP. Template DNA was denatured at 94° C. for 7 minutes. The amplification was carried out in a Perkin-Elmer thermocycler for 25–35 cycles. Each cycle consists of a denaturation step set at 94° C. for 1 min, an annealing step at 55° C. for 2 min and an extension step at 72° C. for 3 min. The denaturation step of the first cycle was extended to 7 min and an extra 72° C., 10 min extension step was included at the end of the cycles. The PCR products were analyzed in an 1–4% agarose gel. Amplified DNA was excised from gel, purified on glass beads (Geneclean) and subcloned into the HincII site of the general purpose cloning vector pBS (Stratgene).

Library Construction & Screening

Human liver mRNA was purchased from Clontech Labs and cDNA was synthesized by the procedure of Gubler and Hoffmann (29). In a 50 μl reaction (50 mM Tris-HCl pH8.3, 75 mM KCl, 3 mM MgCl$_2$, 10 mM DTT, 0.5 mM dATP, 0.5 mM dCTP, 0.5 mM dGTP, 0.5 mM dTTP), 1 μg of mRNA primed with 1.25 μg oligo-dT was converted into single stranded cDNA using the RNAseH negative MMLV-reverse transcriptase (BRL). The reaction was incubated at 37° C. for 1 hour. The yield was monitored by adding 10 μCi $^{32}$P- dCTP to the reaction and measuring incorporated radioactivity after TCA precipitation.

Second strand synthesis was carried out as follow using buffers from the Amersham cDNA synthesis and cloning kit. The 250 μl-reaction contains 50 μl of 1st strand synthesis reaction, 93.5 μl 2nd strand synthesis buffer, 4U RNaseH, 115U DNA polymerase I and 91.5 μl water. The synthesis was carried out at 14° C. for 1 hr, then at room temperature for 1 hr followed by an 10-min incubation at 70° C. 2 μl T4 DNA polymerase (4 U/μl) was added and the mix incubated for 10 min at 37° C. The yield of the reaction was estimated by counting TCA precipitated cDNA. Purified double-stranded cDNA was methylated in a 20-μl reaction containing 4 ml of M buffer, 1× s-adenosylmethionine and 30U of EcoRI methylase. The mixture was incubated at 37° C. for 1 hr and then 10 min at 70° C. to inactivate the enzyme. EcoRI linkers (1.5 μg) were ligated to methylated cDNA (1.5 μg) in an overnight reaction at 15° C. in 50 μM Tris-HCl pH7.5, 10 mM MgCl2, 10 mM DTT, 1 mM ATP and T4 DNA ligase. The linkered cDNA was digested with EcoRI (100U) in a 100 μl reaction for 5 hrs at 37° C. Digested cDNA was then size fractionated in a Sephacryl S500 column and high molecular weight fractions were pooled and purified.

The gene library was constructed in the vector, lambda ZAPII Strategen). cDNA was ligated to the EcoRI-digested phosphorylated vector overnight at 14° C. in a 10 μl reaction containing T4 DNA ligase and its buffer. Ligated cDNA was packaged into phage using the Gigapack kit under conditions suggested by Stratagene.

A library of 2.5 million clones was generated and plated out on XL-1 blue cells and duplicate set of filters was lifted. The procedure for plaque hybridization of Benton & Davis(26) was followed. A radioactive $^{32}$P labelled DNA probe ($2.5 \times 10^8$ cpm/μg) was prepared by the random priming method (27). Hybridization was carried out in 6×SSC, 0.1% SDS, 5× Denhardt's, 100 μg/ml salmon sperm DNA, 25–50% formamide at 42° C. overnight. The filters were washed in 0.1–2× SSC, 0.1% SDS at 37° C. (low stringency) or 55° C. (high stringency) before autoradiography.

DNA Sequencing

Double stranded plasmid DNA was sequenced according to the procedure described in the Sequenase (USB) manual. FIG. 9 shows the nucleotide sequence and translated amino acid sequence of the human liver GPI-PLD. FIG. 10 shows the alignment of amino acid sequence of the human and bovine liver GPI-PLD mature protein.

EXAMPLE 5

Isolation and Characterization of a Human Pancreatic Phospholipase D cDNA Clone

Total RNA was isolated from a human pancreas tumor as described by Gubler et al., Proc. Natl. Acad. Sci. U.S.A. 80, 4311–4314. Poly A+ RNA was selected resulting in a yield of 2.5% (w/w) relative to the total amount of RNA input. A cDNA library was constructed in λgt 11 and amplified according to procedures published in Sambrook, J., Fritsch, E. F. and Maniatis, T., Molecular Cloning, A Laboratory Manual, Second Edition, Cold Spring Harbor Laboratory Laboratory Press 1989. The cDNA library was screened using the bovine GPI-PLD nick-translated cDNA as a probe [see Kochan, J. et al. (1986) Cell 44, 689–696] under conditions of reduced stringency (25% formamide). Two positive clones were plaque purified, cDNA inserts were subcloned in pGem3z (Promega Biotec) and their sequence determined using the dideoxy sequencing technique as recommended by the manufacturer of sequenase (United States Biochemical Corp.) The sequence of clone pJJ1935a is shown in FIG. 11 and begins at nucleotide 1 (corresponding to nucleotide 1609 of the bovine GP-PLD nucleotide). The sequence of clone pJJ1939 begins at nucleotide position 410 of pJJ1935a and is identical to pJJ1935a.

Analysis of the partial amino acid sequence of the human pancreas GPI-PLD reveals a high level of identity (81%) when compared to the bovine amino acid sequence, and 84% identity at the nucleotide level.

EXAMPLE 6

Novel Process for the Production of Recombinant, Secretable Proteins

Other proteins that are normally not GPI-anchored can be made to be GPI-anchored by modifying their genes to encode the signal sequence for GPI-attachment at their 3' ends. If cells are transfected with both this modified gene and the gene for GPI-PLD, the protein is secreted.

To determine if the principle of GPI-anchor protein secretion could be applied in general to other proteins, the GPI-anchor of CD16 was transferred to other proteins, and their expression was monitored in the presence or absence of GPI-PLD. A DNA fragment encoding the portion of CD16 that signals GPI attachment (38–40).

Ser Thr Ile Ser Ser Phe Ser Pro Pro Gly Tyr Gln Val Ser Phe
21
Cys Leu Val Met Val Leu Leu Phe Ala Val Asp Thr Gly Leu
37
Tyr Phe Ser Val Lys Thr Asn Ile, was spliced to DNA encoding the extracellular domains of the Endothelial Leukocyte Adhesion Molecule-1 (ELAM-1) (44); and to DNA encoding the extracellular domains of the p70 subunit of the IL-2 receptor (48) by general methods common to the art.

Specifically for the ELAM-1, two independent constructs were made using PCR technology, namely, ELAM-1-1-GPI and ELAM-1-2-GPI. For ELAM-1-1-GPI the oligonucleotide 540 -TTTGATCATTCTCT-CAGCTCTCACTTTG-3' (5' sense primer) and 5'-TGGTCGACTCAGTGGGAGCTTCACAGGT-3' (3' anti-sense primer) were used to generate an amplicon. This amplicon was then digested with the restriction enzymes BclI and SalI and contained the ELAM extracellular coding sequences (amino acids 15-532) used for the ELAM1-GPI construct. For ELAM-1-2-GPI, the oligonucleotides 5'-TTTGATCATTCTCT-CAGCTCTCACTTTG-3' (5' sense primer) and 5'-TAGTCGACACAATTTGCTCACACTTGAG-3' (3' anti-sense primer) were used to generate an amplicon. This amplicon was then digested with the restriction enzymes BclI and SalI and contained the ELAM-1 extracellular coding sequences (amino acids 15-157) used for the ELAM-1-2-GPI construct.

For p70-GPI the oligonucleotides 5'-ACGTCGACGTGTCCTTCCCAAGGGCTGC-3', (3' anti-sense primer) and 5'-CCGGATCCTGTCCTGGCGTCTGCCCCTC3' (5' sense primer) were used to generate an amplicon. This amplicon was digested with the restriction enzymes BamHI and SalI and contained th p70 extracellular coding sequences (amino acids 21-214) used for the p70-GPI construct. The C-terminal GPI signal peptide from CD16 was also isolated by using PCR technology. The oligonucleotides 5'-GTGTCGACCATCTCAT-CATTCTCTCCA-3' (5' sense primer) and 5'-AGTGTTTGTGTAGCTCTGAAACTT-3', (3' antisense primer) were used to generate an amplicon, which was digested with the restriction enzymes SalI and StuI (internal site in the amplicon) and encoded amino acids 180-216 of the CD16 protein. To generate the various GPI chimeric constructs, the protein coding regions of the protein of interest were ligated to the CD16 GPI-anchor sequences and in turn ligated into the eukaryotic expression vector pBC12BI (which had been digested with BamHI and SmaI). The different GPI-constructs were identified by colony hybridization, and verified by restriction enzyme analysis and DNA sequencing.

To determine if the hybrid GPI-proteins were secreted when co-transfected with the GPI-PLD, COS cells were transfected with ELAM-1-1-GPI (FIG. 12A), ELAM-1-2-GPI (FIG. 12B) or p70-GPI in the presence or absence of pBJ1682. Two days after transfection, the cells were metabolically labelled with $^{35}S$-cysteine for two hours. The cell media or extracts were immunoprecipitated using antibodies directed against the protein of interest, fractionated by SDS-PAGE and visualized by fluorography. The protein of interest was detected in all of the cell extracts we examined but was only found in the supernatant when the GPI-PLD construct was co-tranfected. These results demonstrate that a GPI-anchor can be attached to a protein which is not normally GPI-anchored, and that this novel hybrid protein can be secreted if it is expressed in the presence of the GPI-PLD enzyme. Such a secreted protein may be therapeutically relevant in the treatment of various diseases depending on the hybrid protein which is used.

EXAMPLE 7

Secretion of Proteins That Are Naturally GPI Anchored When Co-Expressed with GPI PLD COS cells transfected with GPI anchored PLAP release much more PLAP into the media when the cells are also transfected with GPI PLD (35). The secreted material was initially detected by measuring alkaline phosphatase activity released into the medium. Similar results were obtained when cells were labeled with $^3H$-ethanolamine, which results in incorporation of $^3H$-label into the GPI moiety (an ethanolamine residue links the COOH-terminal amino acid of the protein via a phosphodiester bond to the glycan complex (30) and the amount of radiolabeled PLAP secreted from cells was compared in the presence of absence of GPI PLD (35). These experiments also demonstrated that the PLAP released in the presence of GPI PLD was not due to proteolytic cleavage, but that it indeed contained a GPI moiety.

One form of a human low affinity IgG receptor, FcGRIII B (or CD16), has been shown to be GPI anchored (38-41). To demonstrate GPI PLD-mediated secretion was not unique to PLAP, COS cells were transfected with CD16 in the presence or absence of GPI PLD, and FcGRIII B expression was monitored. Transfected cells were then labeled with $^3H$-ethanolamine and both the cell extracts and media incubated with anti-CD16 mAb 3G8 (42) to immunoprecipitate CD16. The immunoprecipitated material was fractionated on an SDS-polyacrylamide gel and autoradiographed. The results showed that radiolabeled CD16 was immunoprecipitated from cell extracts regardless of whether GPI PLD was expressed, but it was immunoprecipated from media only when co-expressed with GPI PLD (FIG. 13). This result was the same as that observed with radiolabeled PLAP (35 and provided another example of a GPI anchored protein that is secreted in the presence of GPI PLD.

EXAMPLE 8

Construction of Chimeric Genes Containing the CD16 GPI Attachment Signal Sequence We sought to test whether proteins that are normally not GPI anchored would become GPI anchored if they contained at their COOH-terminus the CD16 GPI attachment signal (PAS) sequence. Although this sequence in CD16 has not been well defined, it has been demonstrated that amino acid $Ser^{203}$ (counting from the initiating Met) is necessary for GPI attachment (43). To generate a DNA fragment containing a functional PAS sequence, yet encoding a minimal portion of CD16, we used PCR to amplify a fragment that would encode amino acids $Ser^{197}$ to $Ile^{223}$ ($Ile^{223}$ is the COOH-terminal amino acid of the initial translation product). This 37 amino acid fragment from CD16 had the following sequence (the underline indicates a hydrophobic stretch of amino acids, characteristic of PAS sequences:

SerThrIleSerSerPheSerProProGlyTyrGln<u>ValSerGlyCysLeuVal</u>
<u>MetValLeuLeuPheAlaValAspThrGlyLeuTyrPheSerVal</u>
LysThrAsnIle

The DNA fragment encoding these 37 amino acids was spliced to DNA encoding extracellular domains of several receptors including: (1) the human endothelial cell-leukocyte adhesion molecule (ELAM-1)(44), (2) the α subunit of the human and rat high-affinity IgE receptor (FcERI)(45, 46), (3) the murine interleukin-1 receptor (IL-1R)(47) and (4) the human p70 subunit of the interleukin-2 receptor (48) (FIG. 14). Two different ELAM-1/CD16 constructs were made with one containing the entire extracellular domain of ELAM-1 (ELAM$_1$/CD16) and a second one containing only the lectin and EGF-like domains of ELAM-1(44) (ELAM$_2$/CD16). DNA coding the PAS sequence of PLAP(36, 37, 49) was also used to make chimeric genes. The PAS amino acid sequence of PLAP started at $Pro^{478}$ and had the following sequence (hydrophobic stretch is underlined):

ProProAlaGlyThrThrAspAlaAlaHisProGlyArg<u>SerValValProAla</u>
<u>LeuLeuProLeuLeuAlaGlyThrLeuLeuLeuLeuGlu</u>ThrAla
ThrAlaPro

These chimeric genes were ligated into the eukaryotic expression plasmid, pBC12BI(50), for expression in COS cells.

EXAMPLE 9

Cell-Surface Expression of Chimeric Gene Products

The native forms of several of the proteins examined are not readily detected on the surface of transfected COS cells for reasons that are not entirely clear. The ability of chimeric gene products to be expressed on the cell surface might be indicative of GPI anchoring.

Therefore, it was determined whether the chimeric gene-products could be expressed on the cell surface of transfected COS cells by indirect immunofluorescence. All proteins examined (see FIG. 14) were expressed at relatively high levels as judged by the intensity of immunofluorescence. This group of proteins included the human and rat FcERIα subunits (FIG. 15) as well as the IL-2R p70 subunit, the truncated ELAM-1 proteins and the IL-1R. The origin of the COOH-terminal PAS (CD16 vs PLAP) did not affect the ability of FcERIα to be expressed at the surface (FIG. 15) suggesting that different PAS sequences could function with similar efficiency.

EXAMPLE 10

Chimeric Proteins are GPI Anchored

The chimeric proteins being expressed on the cell surface are demonstrably GPI anchored. Transfected COS cells were metabolically labeled with $^3$H-ethanolamine. The recombinant proteins were immunoprecipitated from cell extracts, fractionated by SDS-PAGE, and analyzed for the incorporation of $^3$H-ethanolamine by fluorography. FIG. 16 (top) shows the results of immunoprecipitating a number of different chimeric proteins (ELAM$_1$, ELAM$_2$, IL-1R and FcERIα). For each of the proteins examined, a radioactively labeled band of the expected size was observed. These bands were detected only from cells transfected with chimeric constructs, and not from cells transfected with either the native, wild-type genes (lanes 1 and 6) or a truncated, secreted form (lane 9). These controls established that the $^3$H-ethanolamine label was specifically incorporated into the chimeric proteins, demonstrating that the proteins were GPI anchored.

EXAMPLE 11

Secretion of Chimeric Proteins When Co-Expressed With GPI PLD

To determine that the chimeric GPI anchored proteins are secreted when co-expressed with GPI PLD, co-transfected COS cells were labeled with $^3$H ethanolamine, and the media was immunoprecipitated. As shown in FIG. 16 (bottom), $^3$H-labeled ELAM$_1$/CD16, ELAM$_2$/CD16, FcERIα/CD16 and IL-1 R/CD16 were immunoprecipitated from the medium when expressed in the presence of GPI PLD, but not in its absence. For several of the chimeric proteins, ELAM$_1$/CD16, ELAM$^2$/CD16, and IL-1 R/CD16, co-transfection with GPI PLD resulted in the appearance of more material immunoprecipitated from the media than the cell extracts (lanes 3, 5 and 11; top vs bottom of FIG. 16). In addition, lower levels of $^3$H-labeled protein were detected in cell extracts in the presence of GPI PLD than in its absence (compare lane 2 vs. lane 3, FIG. 16 top). Together, these results show that GPI PLD-mediated secretion of these three chimeric proteins was reasonably efficient. In contrast, relase of the FcERIα/CD16 appeared less efficient.

The ability of GPI PLD to mediate secretion of chimeric GPI anchored proteins was independently demonstrated by labeling ELAM$_1$/CD16- or ELAM$_2$/CD16-transfected cells with $^{35}$S-cysteine and assaying the media for $^{35}$S-labeled proteins by immunoprecipitations. The results confirmed the observations with the $^3$H-ethanolamine label, showing the presence of labeled ELAM in the media when co-transfected with GPI PLD (FIG. 17). Finally, co-transfection of either ELAM$_1$/CD16, ELAM$_1$/PLAP with GPI PLD demonstrated that the PAS sequences from both CD16 and PLAP resulted in the secretion of ELAM$_1$.

Analysis of $^{35}$S-cysteine labeled COS cells transfected with FcERIα/CD16 in the presence of GPI PLD failed to reveal the presence of FcERIα in the medium following a 2 hour pulse (FIG. 18 panel, A, Media). However, if the cells were chased for 16 hours (panel B), labeled FcERIα was readily detected in the medium (FIG. 18). The observation that $^{35}$S-labeled FcERIα was released into the medium in the absence of GPI PLD suggests that FcERIα can also be released via a proteolytic mechanism. Consistent with this prediction was the observation that FcERIα released in the absence of GPI PLD was not labeled with $^3$H-ethanolamine (FIG. 16). The action of a protease would result in the loss of the $^3$H-ethanolamine label in FcERIα.

Release of FcERIα in the absence of GPI PLD was confirmed by assaying media for the presence of the FcERIα subunit in an IgE binding assay. Two different FcERIα chimeric GPI anchored molecules, FcERIα/CD16 and FcERIα/PLAP, were transfected into COS cells in the presence or absence of GPI PLD (FIG. 19). Expression of wild type FcERIα or a hybrid FcERIα (52) in COS cells did not result in the release of any IgE binding activity. Expression of the chimeric FcERIα GPI anchored molecules resulted in the release of material that exhibited IgE binding activity even in the absence of GPI PLD (FIG. 19). The levels of IgE binding activity released were increased two to four fold when GPI was co-transfected with the chimeric GPI anchored FcERIα molecules. The presence of serum in the culture medium did not affect the levels of FcERIα released, as identical amounts of FcERIα were released in serum-free medium. Similar results were observed when the secretion of IL-1 R was assayed in the presence or absence of GPI PLD.

It should be noted that the secreted proteins may include several amino acids from the PAS sequence (e.g., of CD16) at their COOH-termini and will have an attached inositol-glycan moiety. For those secreted proteins that were tested for their functional activity, there was no indication of impaired function, e.g., the FcERIα still bound IgE and secreted IL-1R still bound IL-1. In addition, the GPI anchor also did not impair function of those chimeric proteins that were tested for ligand binding while anchored to the cell surface. Both ELAM$_1$/CD16 and ELAM$_2$/CD16 expressed on the surface of COS cells mediated efficient binding of HL60 cells (a human promyelocytic cell line that expressed the ELAM-1 ligand on its cell surface) to the transfected COS cells. Additionally, our studies with the FcERIα clearly demonstrate that these proteins retain their ability to bind IgE, when anchored to the cell surface by a GPI moiety, or when released into the media by the action of either GPI PLD or a putative proteolytic mechanism.

FcERIα/CD16 and IL-R/CD 16 were observed to be secreted in the absence of GPI-PLD, but at much lower levels than in its presence.

REFERENCES

1. Low, M. G., and Saltiel, A. R. (1988) *Science*, 239, 268–275.
2. Low, M. G. (1987) *Biochem. J.*, 244, 1–13
3. Ferguson, M. A. J., and Williams, A. F. (1988) *Annu. Rev. Biochem.*, 57, 285–320

4. Low, M. G. (1989) *Biochem. Biophys. Acta,* 988, 427–454

5. Malik, A.-S. and Low, M. G. (1986) *Biochem. J.,* 240, 519–527

6. Low, M. G., and Prasad, A. R. S. (1988) *Proc. Natl. Acad. Sci. USA,* 85, 980–984

7. Davitz, M. A., Hereld, D., Shak, S., Krakow, J., Englund, P. L., and Nussenzweig, V. (1987) *Science,* 238, 81–84

8. Cardoso de Almeida, M. L., Turner, M. J., Stambuk, B. B. and Schenkman, S. (1988) *Biochem. Biophys. Res. Commun.,* 150, 476–482

9. Huang, K.-S., Li, S. and Low, M. G. (1991) *Methods Enzymol.,* 197, 567–575

10. Hereld, D., Krakow, J. L., Bangs, J. D., Hart, G. W., and Englund, P. T. (1986) *J. Biol. Chem.,* 261, 13813–13819

11. Low, M. G., Stiernberg J., Waneck, G. L., Flavell, R. A., and Kincade, P. W. (1988) *J. Immunol. Methods,* 113, 101–111

12. Bradford, M. (1976) *Anal. Biochem.,* 72, 248–254

13. Hunkapillar, M. W., Lujan, E., Ostrader, F., and Hood, L. E. (1983) *Methods Enzymol.,* 91, 227–236

14. Thomas, P. E., Reik, L. M., Ryan, D. E., and Levin, W. (1984) *J. Biol. Chem.,* 259, 3890–3899

15. Reik, L. M., Maines, S. L., Ryan, D. E., Levin, W., Bandiera, S., and Thomas, P. E. (1987) *J. Immunol. Methods,* 100, 123–130

16. Towbin, H., Staehlin, T., and Gordon, J. (1979) *Proc. Natl. Acad Sci. USA,* 76, 4350–4354

17. Nielsen, P. J., Manchester, K. L., Towbin, H., Gordon, J., and Thomas, G. (1982) *J. Biol. Chem.,* 257, 12316–12321

18. Laemmli, U. K. (1970) *Nature,* 227, 680–685

19. Hynes, R. O. (1987) *Cell,* 48, 549–554

20. Ponez, M., Eisman, R., Heidenreich, R., Silver, S. M., Vilaire, G., Surrey, E., Schwartz, E., and Bennet, J. S. (1987) *J. Biol. Chem.,* 262, 8476–8482

21. Argraves, W. S., Suzuki, S., Arai, H., Thompson, K., Pierschbacher, M.D., and Ruoslahti, E. (1987) *J. Cell Biol.,* 105, 1183–1190

22. Suziki, S, Argraves, W. S., Arai, H., Languino, L. R., Pierschbacher, M. D., and Ruoslahti, E. (1987) *J. Biol. Chem.,* 262, 14080–14085

23. Kretsinger, R. H. (1976) *Annu. Rev. Biochem.,* 45, 239–266

24. Herzberg, O., and James, M. N. G. (1985) *Biochemistry,* 24, 5298–5302

25. Davitz, M. A., Hom, J., and Schenkman, S. (1989) *J. Biol. Chem.,* 264, 13760–13764

26. Benton & Davis, Science, 196 (1977), 180

27. Feinberg & Vogelstein, *Anal. Biochem,* 137, (1984) 267

28. Saiki R. K., Gelford D. H., Stoffel S., Schanf S. J., Higudn, R. Horn G. T., Mullis K. B. & Erlich H. A., Science 239, 487–494 (1988)

29. Gubler U and Hoffmann B. J., *Gene* 25, 263 (1983)

30. Thomas, J. R., Dwek, R. A., and Rademacher, T. W. 1990. Structure, biosynthesis, and function of glycosyl-phosphatdylinositol. Biochem. 29:5413:5422.

31. Doering, T. L., Masterson, W. J., Hart, G. W., and Englund, P. T., 1990. Biosynthesis of glycosyl-phosphatidylinositol membrane anchors. *J. Biol. Chem.* 265:611–614.

32. Low, M. G. 1989. Glycosyl-phosphatidylinositol: a versatile anchor for cell surface proteins. *FASEB J.* 3:1600–1608.

33. Cross, G. A. M. 1990. Glycolipid Anchoring of Plasma Membrane *Proteins.* Ann. Rev. Cell Biol. 6:1–39.

34. Lisanti, M. P., Caras, I. W., Davitz, M. A., and Rodriguez-Boulan, E. 1989. A glycophospholipid membrane anchor acts as an apical targeting signal in polarized epithelial cells. *J. Cell. Biol.* targeting signal in polarized epithelial cells. *J. Cell Biol.* 109:2145–2156.

35. Scallon, B., Fung, W. J., Tsang, C., Li, S., Kado-Fong, H., Huang, K. S., and Kochan, J., 1991. Primary structure and functional activity of phosphatidylinositol-glycan-specific phospholipase D. *Science* 252:446–448.

36. Howard, A. D., Berger, J., Gerber, L., Familetti, P., and Udenfriend, S. 1987. Characterization of the phosphatidylinositol-glycan membrane anchor of human placental alkaline phosphatase. *Proc. Natl. Acad. Sci.* USA 84:6055–6059.

37. Jemmerson R., and Low, M. G. 1987. Phosphatidylinositol anchor of HeLa cell alkaline phosphatase. *Biochem.* 26:5703–5709.

38. Selvaraj, P., Rosse, W. F., Silber, R., and Spinger, T. A. 1988. The major Fc receptor in blood has a phosphatidylinositol anchor and is deficient in paroxysmal nocturnal haemoglobinuria. *Nature* 333:565–567.

39. Simmons, D. and Seed, B. 1988. The Fcγ receptor of natural killer cells is a phopholipid-linked membrane protein. *Nature* 333:568–570.

40. Scallon, B. J., Scigliano, E., Freedman, V. H., Miedel, M. C., Pan, Y.-C., Unkeless, J. C., and Kochan, J. P., 1989. A human immunoglobulin G receptor exists in both polypeptide-anchored and phosphatidylinositol-glycan-anchored forms. *Proc. Natl. Acad. Sci.* USA 86:5079–5083.

41. Ravetch, J. V., and Perussia, B. 1989. Alternative membrane forms of FcGRIII (CD16) on human natural killer cells and neutrophils. *J. Exp. Med.* 170:481–497.

42. Fleit, H. B., Wright, S. D., and Unkeless, J. C. 1982. Human neutrophil Fc receptor distribution and function. *Proc. Natl. Acad. Sci.* USA 79:3275–3279.

43. Kurosaki, T., and Ravetch, J. V. 1989. A single amino acid in the glycosyl-phosphatidylinositol attachment domain determines the membrane topology of FcGRIII. *Nature* 342:805–807.

44. Bevilacqua, M. P., Stengelin, S., Gimbrone, M. A., Jr., Seed, B. 1989. Endothelial leukocyte adhesion molecule 1: an inducible receptor for neutrophils related to complement regulatory proteins and lectins. *Science* 243:1160–1165.

45. Kochan, J. P., Pettine, L. F., Hakimi, J., Kishi, K., and Kinet, J. P., 1988. Isolation of the gene coding for the alpha subunit of the human IgE receptor. *Nuc. Acids Res.* 16:3584.

46. Kinet, J. P., Metzger, H., Hakimi, J., and Kochan J. 1987. A cDNA presumptively coding for the α subunit of the receptor with high affinity for Immunoglobulin E. Biochemistry 26:4605–4610.

47. Sims, J. E., March, C. J., Cosman, D., Widmer, M. B., MacDonald, H. Robson, McMahan, C. J., Grubin, C. E., Wignall, J. M., Jackson, J. L., Call, S. M., Friend, D. Alpert, A. R. Gillis, S. Urdal, D. L., and Dower, S. K. 1988. cDNA expression cloning of the IL-1 receptor, a member of the immunoglobulin superfamily. *Science* 241:585–589.

48. Hatakeyama, M., Tsudo, M., Minamoto, S., Kono, T., Doi, T., Miyata, T., Miyasaka, M., and Taniguchi, T. 1989. Interleukin-2 receptor β chain gene: generation of three receptor forms by cloned human α and β chain cDNA's. Science 244:551–556.

49. Kam, W., Clauser, E., Kim, Y. S., Kan, Y. W., and Rutter, W. J. 1985. Cloning, seqencing, and chromosomal localization of human term placental alkaline phosphatase cDNA. Proc. Natl. Acad. Sci. USA 8715–8719.

50. Cullen, B. R., 1987. Use of eukaryotic expression technology in the functional analysis of cloned genes. In Methods Enzymol. 152:684–704.

51. Lin, A. Y., Devaux, B., Green A., Sagerstrom, C., Elliot, J. F., and Davis M. M., 1990. Expression of T cell antigen receptor heterodimers in a lipid-linked form. Science, 249:677–679.

52. Hakimi, J., Seals, C., Kondas, J. A., Pettine, L., Danho, W., and Kochan, J. 1990. The a subunit of the human IgE receptor (FcERI) is sufficient for high affinity IgE binding. J. Biol. Chem. 265:22079–22081.

53. Riske, F., Hakami, J. Mallamaci, M., Griffin, M., Pilson, B., Tobkes, N., Lin, P., Danho, W. Kochan, J. and Chizzonite, R. 1991. High affinity human IgE receptor (FcεRI): Analysis of functional domains of the α-subunit with monoclonal antibodies J. Biol. Chem. 266:111245–11251.

54. Ravetch, J. V., and Kinet, J.-P. 1991. Fc Receptors. Ann. Rev. Immunol. 9:457–492.

We claim:

1. An isolated gene which encodes the protein glycosyl-phosphatidylinositol-specific phospholipase D and has the nucleotide sequence of FIG. 5.

2. An isolated gene which encodes the protein glycosyl-phosphatidylinositol-specific phospholipase D and has the nucleotide sequence of FIG. 9.

3. A synthetic polynucleotide molecule expressing a protein which is connected to a glycosyl-phosphatidylinositol anchor molecule, which polynucleotide molecule comprises both a first nucleotide sequence encoding glycosyl-phosphatidylinositol-specific phospholipase D, and a second nucleotide sequence encoding said protein to be expressed, said second nucleotide sequence being directly linked at its 3' end to a third nucleotide sequence encoding a C-terminal signal peptide obtained from a GPI anchored protein, which C terminal signal peptide directs the attachment of a glycosyl-phosphatidyl inositol anchor molecule to the protein to be expressed.

4. The synthetic polynucleotide molecule of claim 2 wherein the third nucleotide sequence encoding a C-terminal signal peptide is derived from the placental alkaline phosphatase gene.

5. The synthetic polynucleotide molecule of claim 3 wherein the third nucleotide sequence encoding a C-terminal signal peptide is derived from the CD16 gene.

6. A vector designed for expressing protein which expresses a protein which is connected to a glycosyl-phosphatidylinositol anchor molecule, which vector contains both a first nucleotide sequence encoding glycosyl-phosphatidylinositol-specific phospholipase D, and a second nucleotide sequence encoding said protein to be expressed said second nucleotide sequence being directly linked at its 3' end to a third nucleotide sequence encoding a C-terminal signal peptide which directs the attachment of a glycosyl-phosphatidyl inositol anchor molecule to the protein to be expressed, such sequences suitably located in the vector so as to express a protein.

7. A transformed host cell which produces glycosyl-phosphatidylinositol anchor molecules, which host cell contains a vector designed for expressing protein-inserted therein comprising a first nucleotide sequence encoding glycosyl-phosphatidyl inositol-specific phospholipase D, and a second nucleotide sequence encoding a protein to be expressed, said second nucleotide sequence being directly linked at its 3' end to a third nucleotide sequence encoding a C-terminal signal peptide which directs the attachment of a glycosyl-phosphatidylinositol anchor molecule to the protein to be expressed, such sequences suitably located in the vector so as to express a protein.

8. A transformed host cell which produces glycosyl-phosphatidylinositol anchor molecules, which host cell contains inserted therein both a first vector designed for expressing protein comprising a first nucleotide sequence encoding glycosyl-phosphatidylinositol-specific phospholipase D, and a second vector designed for expressing protein comprising a second nucleotide sequence encoding a protein to be expressed, said second nucleotide sequence being directly linked at its 3' end to a third nucleotide sequence encoding a C-terminal signal peptide which directs the attachment of a glycosyl-phosphatidylinositol anchor molecule to the protein to be expressed, such sequences suitably located in the vectors so as to express proteins.

9. A process for producing a protein which comprises:

a. providing a host cell which produces glycosyl-phosphatidylinositol anchor molecules;

b. inserting into said host cell by means of vectors designed for expressing protein to produce a transformed host cell, a synthetic polynucleotide molecule expressing a protein which is connected to a glycosyl-phosphatidylinositol anchor molecule, which polynucleotide molecule comprises both a first nucleotide sequence encoding glycosyl-phosphatidylinositol-specific phospholipase D, and a second nucleotide sequence encoding the protein to be produced, said second nucleotide sequence being directly linked at its 3' end to a third nucleotide sequence encoding a C-terminal signal peptide which directs the attachment of a glycosyl-phosphatidylinositol anchor molecule to said protein to be produced, such sequences suitably located in the vectors so as to express proteins; and c. incubating said transformed host cell in medium to cause said host cell to express said protein, whereby said protein is produced in the medium.

* * * * *

UNITED STATES PATENT AND TRADEMARK OFFICE
CERTIFICATE OF CORRECTION

PATENT NO. : 5,418,147
DATED : May 23, 1995
INVENTOR(S) : Huang, et al.

It is certified that error appears in the above-indentified patent and that said Letters Patent is hereby corrected as shown below:

Column 33, line 50, delete "claim 2" and insert --claim 3--.

Signed and Sealed this

Fifteenth Day of August, 1995

Attest:

BRUCE LEHMAN

Attesting Officer     Commissioner of Patents and Trademarks